US012734323B2

(12) United States Patent
Patel et al.

(10) Patent No.: US 12,734,323 B2
(45) Date of Patent: Sep. 15, 2026

(54) PATIENT INTERFACE AND RESPIRATORY SUPPORT APPARATUS

(71) Applicant: Fisher & Paykel Healthcare Limited, Auckland (NZ)

(72) Inventors: Roheet Patel, Auckland (NZ); Daylin Alvares, Auckland (NZ); Matthew Ivan Small, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 690 days.

(21) Appl. No.: 18/245,823

(22) PCT Filed: Aug. 24, 2021

(86) PCT No.: PCT/NZ2021/050145
§ 371 (c)(1),
(2) Date: Mar. 17, 2023

(87) PCT Pub. No.: WO2022/066023
PCT Pub. Date: Mar. 31, 2022

(65) Prior Publication Data
US 2023/0338687 A1 Oct. 26, 2023

Related U.S. Application Data

(60) Provisional application No. 63/203,563, filed on Jul. 27, 2021, provisional application No. 63/084,379, filed on Sep. 28, 2020.

(51) Int. Cl.
*A61M 16/06* (2006.01)

(52) U.S. Cl.
CPC .... *A61M 16/0622* (2014.02); *A61M 16/0605* (2014.02); *A61M 16/0616* (2014.02)

(58) Field of Classification Search
CPC .............. A61M 16/06; A61M 16/0605; A61M 16/0611; A61M 16/0616; A61M 16/0622; A62B 18/02; A62B 18/025
See application file for complete search history.

(56) References Cited

U.S. PATENT DOCUMENTS 2,403,046 A 7/1946 Bulbulian
2,415,846 A 2/1947 Randall
(Continued)

FOREIGN PATENT DOCUMENTS

WO WO 99/21602 A1 5/1999
WO WO 2006/074514 A1 7/2006
(Continued)

OTHER PUBLICATIONS

International Search Report for International Patent Application No. PCT/NZ2021/050145, dated Nov. 23, 2021 in 4 pages.
(Continued)

*Primary Examiner* — Joseph D. Boecker
(74) *Attorney, Agent, or Firm* — VIA LLP

(57) ABSTRACT

A patient interface is provided for use with a respiratory support apparatus, and comprises: a. a cushion at least partially defining an internal cavity, the cushion comprising a pair of opposing cushion side walls and a sealing flange arranged to seal against the face of the patient; b. a gases inlet in fluid communication with the internal cavity; c. a tether; wherein the tether extends substantially laterally across the cushion inside the internal cavity between the pair of opposing cushion side walls, the tether being mounted to the cushion side walls. The tether is configured to allow the cushion to compress when subject to lateral forces, for example when a patient is side sleeping. The tether is configured to resist laterally outward deformation of the cushion.

17 Claims, 32 Drawing Sheets

(56) References Cited

U.S. PATENT DOCUMENTS

| | | | | |
|---|---|---|---|---|
| 10,603,456 | B2 | 3/2020 | Bearne et al. | |
| 10,751,497 | B2 | 8/2020 | Stephens et al. | |
| 10,758,697 | B2 | 9/2020 | Grashow et al. | |
| 11,534,566 | B2 | 12/2022 | Spear et al. | |
| 2009/0159084 | A1* | 6/2009 | Sher | A61M 16/0666 128/205.24 |
| 2012/0167892 | A1* | 7/2012 | Matula, Jr. | A61M 16/06 128/206.21 |
| 2012/0305001 | A1* | 12/2012 | Tatkov | A61M 16/0006 128/205.25 |
| 2014/0366886 | A1* | 12/2014 | Chodkowski | A61M 16/06 128/206.24 |
| 2015/0273171 | A1 | 10/2015 | Sullivan et al. | |
| 2016/0158474 | A1* | 6/2016 | Harrison | A61M 16/0683 128/205.28 |
| 2017/0326319 | A1 | 11/2017 | Stephenson et al. | |
| 2017/0368288 | A1* | 12/2017 | Stephens | A61M 16/0622 |
| 2018/0200468 | A1 | 7/2018 | Chodkowski | |
| 2019/0217036 | A1* | 7/2019 | Spear | A61M 16/0683 |
| 2019/0298958 | A1* | 10/2019 | O'Connor | A61M 16/0666 |
| 2022/0072343 | A1* | 3/2022 | Chi | A62B 23/02 |

FOREIGN PATENT DOCUMENTS

| | | | |
|---|---|---|---|
| WO | WO 2008/037031 | A1 | 4/2008 |
| WO | WO 2015/092723 | A1 | 6/2015 |
| WO | 2015193821 | A1 | 12/2015 |

OTHER PUBLICATIONS

Written Opinion for International Patent Application No. PCT/NZ2021/050145, dated Nov. 23, 2021 in 7 pages.

* cited by examiner

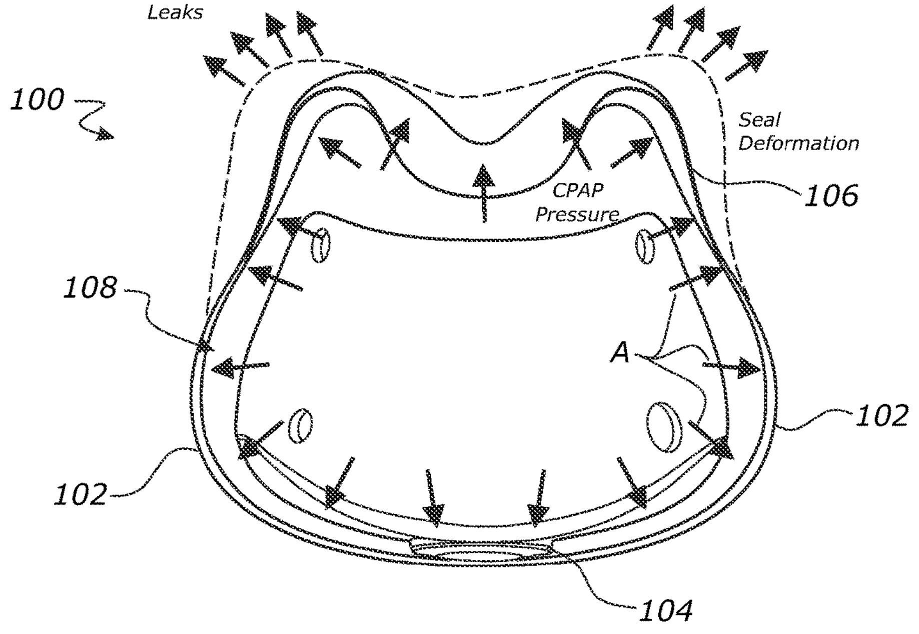
FIGURE 1c
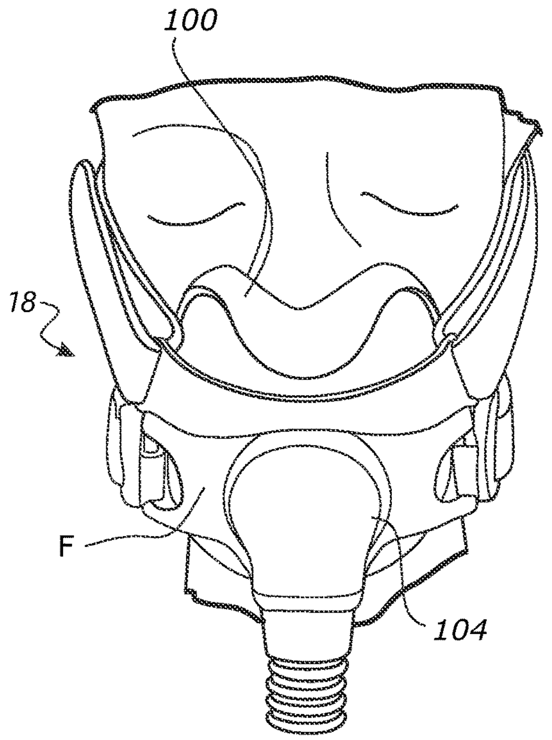
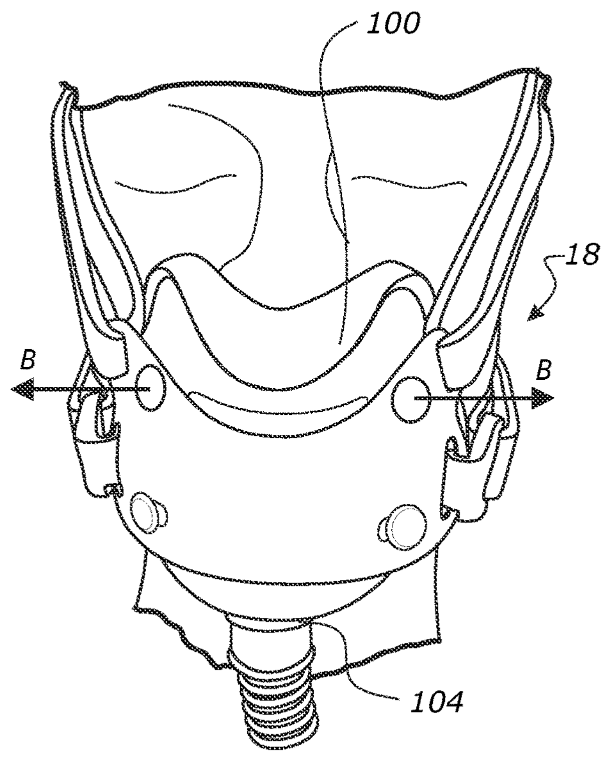
FIGURE 2a
FIGURE 2b

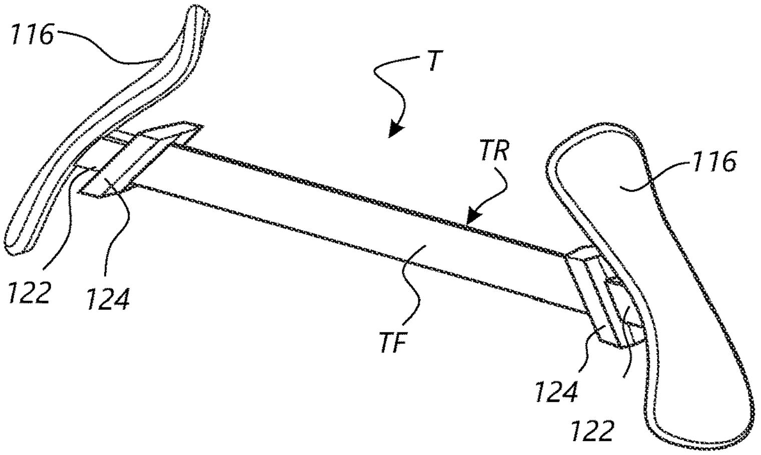
FIGURE 10a
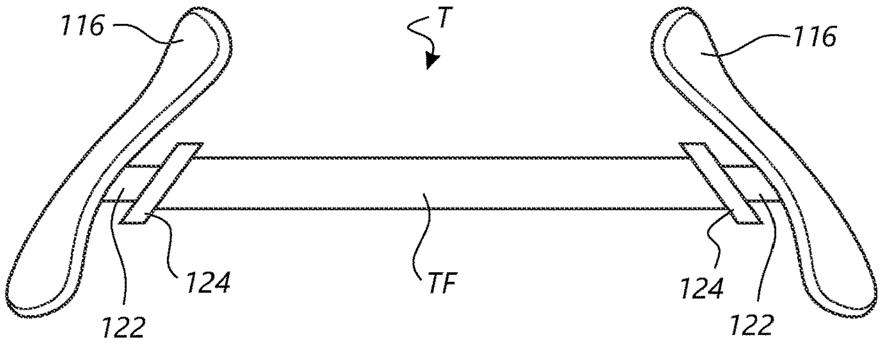
FIGURE 10b
FIGURE 11
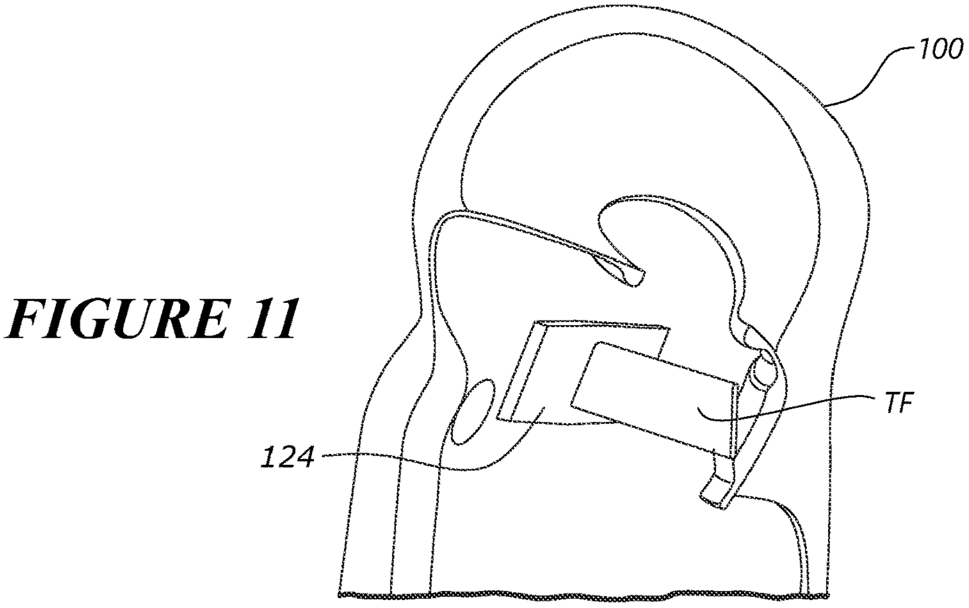

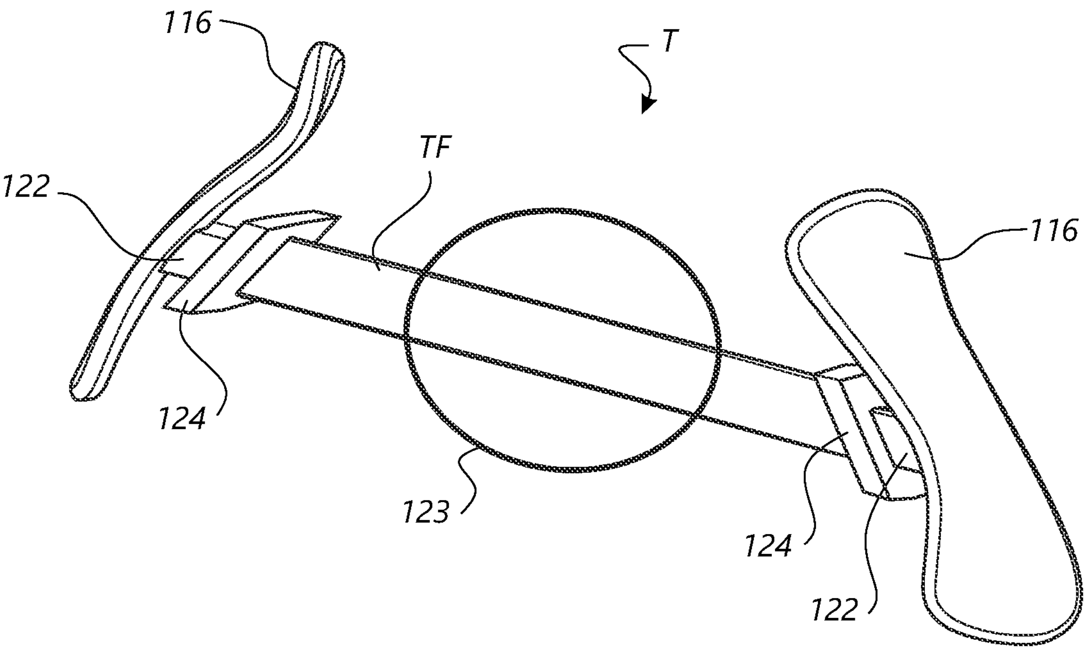
FIGURE 12a
FIGURE 12b
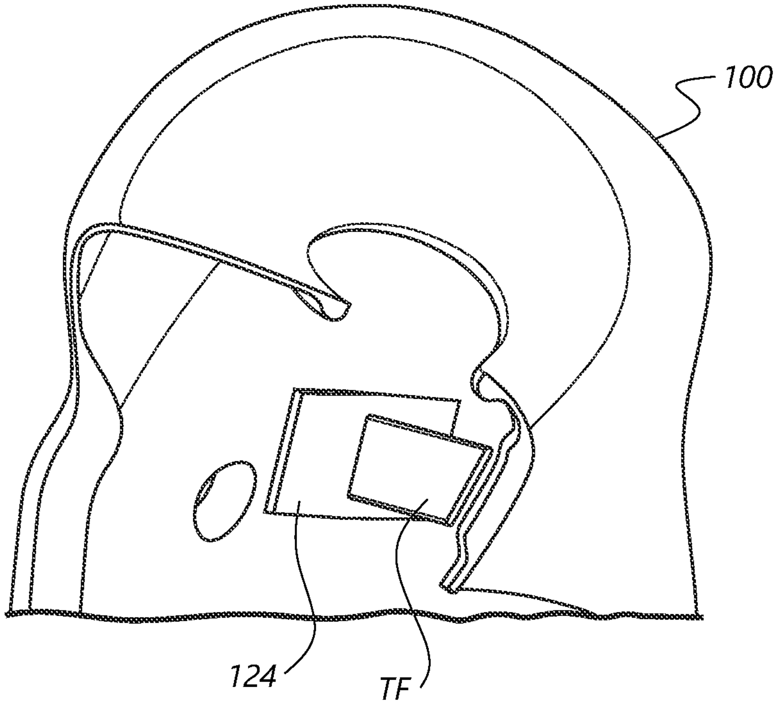

PATIENT INTERFACE AND RESPIRATORY SUPPORT APPARATUS

BACKGROUND OF THE DISCLOSURE

Field of the Disclosure

The present disclosure generally relates to a patient interface for use with, or comprising part of, a respiratory support apparatus configured to provide a breathable gases flow to a patient. The present application is a 371 of International Patent Application No. PCT/NZ2021/050145, filed on Aug. 24, 2021, which claims priority from U.S. provisional patent application 63/084,379 filed 28 Sep. 2020 and U.S. provisional patent application 63/203,563 filed 27 Jul. 2021, both of which are incorporated herein by reference in their entirety.

Description of the Related Art

Respiratory support apparatus are used in various environments such as hospital, medical facilities, residential care, or home environments to deliver a gases flow to a patient. Respiratory support apparatus typically comprise a flow generator to generate a breathable gases flow, and/or are configured to receive a gases flow from an external gases source, such as a hospital oxygen supply for example. The gases flow is delivered to the patient via an inspiratory conduit and a patient interface, the patient interface being mounted on the head of the patient, for example using headgear. Examples of such respiratory support apparatus include CPAP, PEEP, Bi-level and High Flow apparatus. Some respiratory support apparatus are configured to selectively deliver more than one type of respiratory therapy, for example CPAP and High Flow therapies.

One example of use of a respiratory support apparatus is for the treatment of obstructive sleep apnea (OSA) by continuous positive airway pressure (CPAP) flow generator systems involving the continuous delivery of pressurized gases to the air-ways of a human via a conduit and a patient interface. Such a patient interface may be any one of the following:

a. a nasal interface configured to seal around the nares or nose of the patient;
b. an oral mask configured to seal around the mouth of the patient; or
c. a full-face mask configured to seal around both the mouth and nose of the patient.

Typically, the patient interface comprises a cushion and a seal which contacts and seals with the face of the patient, to create at least a substantial seal on or around the nose and/or the mouth. The seal is typically integral with the cushion. It is desirable that the cushion is maintained in the desired position on the patient's head, and that the seal is maintained.

SUMMARY OF THE DISCLOSURE

An example of a respiratory support apparatus in accordance with this disclosure is a CPAP/BiLevel apparatus being a pressure controlled apparatus that attempts to deliver a set pressure. Set pressure may be a constant pressure (CPAP) or may be BiLevel pressure where the two pressures are used, one for inspiration, the other for expiration. It is also possible to deliver a gases flow at a target flow rate rather than pressure, that is, the apparatus is controlled to flow rather than pressure. The apparatus may comprise, or be configured for use with, a patient interface comprising a cushion, and a seal which seals against the patient's face. The cushion and seal may be integral, or separate components. The cushion receives the gases flow from the apparatus.

It is an object of the present disclosure to provide a respiratory support apparatus that provides improved comfort and/or sealing performance, and/or that will at least provide the public and/or the medical profession with a useful choice.

Accordingly in one aspect the disclosure may broadly be said to consist in a patient interface comprising a cushion having side walls, wherein lateral movement of the side walls is controlled. In embodiments in accordance with this disclosure, the lateral movement of the cushion side walls is controlled such that the cushion side walls are prevented, or at least resisted, from moving apart.

Accordingly in an aspect the disclosure may broadly be said to consist in a patient interface comprising a cushion having side walls, wherein the cushion comprises a lateral dimension or width, between the side walls, wherein the cushion controls, and/or resists, and/or in some examples prevents an increase of, the lateral dimension.

Accordingly in one aspect the disclosure may broadly be said to consist in a patient interface comprising a cushion having side walls, and further comprising a tether, configured to extend between and be secured to the side walls. In some embodiments the tether is configured to extend between the side walls below the nose of the patient. In some embodiments the tether is configured to extend between the side walls along the upper lip of the patient.

In aspects of this disclosure there is provided a cushion comprising side walls and a tether extending between the side walls, the tether preventing lateral movement of the side walls away from one another, but allowing lateral movement of the side walls towards one another.

According to an aspect of this disclosure there is provided a patient interface for use with a respiratory support apparatus for delivering breathable gases to a patient, the patient interface comprising;

a. a cushion comprising a pair of opposing cushion side walls; and
b. a tether which extends between, and connects the cushion side walls.

The side walls, when in a rest condition in which a flow of breathable gases is not provided to the patient interface, may be spaced apart a predetermined distance. The tether may resist an increase to that predetermined distance. The tether may therefore resist one or both cushion side walls from moving away from the other cushion side wall. The tether may be further configured to allow one or both cushion side walls to move towards the other cushion side wall.

According to an aspect of this disclosure there is provided a patient interface for use with a respiratory support apparatus for delivering breathable gases to a patient, the patient interface comprising;

a. a cushion at least partially defining an internal cavity, the cushion comprising a pair of opposing cushion side walls and a sealing flange arranged to seal against the face of the patient;
b. a gases inlet in fluid communication with the internal cavity;
c. a tether;

wherein the tether extends substantially laterally across the cushion inside the internal cavity between the pair of opposing cushion side walls, the tether being secured to the cushion side walls.

According to another aspect of this disclosure there is provided a patient interface for use with a respiratory support apparatus for delivering breathable gases to a patient, the patient interface comprising;

a. a flexible cushion comprising:
   i. an internal cavity;
   ii. a face-contacting seal arranged to seal against the face of the patient; and
   iii. non-face contacting cushion side walls;
b. a gases inlet in fluid communication with the internal cavity;
c. an elongate, flexible tether; wherein the tether:
   extends substantially laterally across the cushion inside the internal cavity between the cushion side walls;
   is secured to the cushion side walls; resists ballooning of the cushion side walls in a direction radially outwardly of the internal cavity;
   allows movement of the cushion side walls in a direction radially inwardly of the internal cavity.

According to a further aspect of this disclosure there is provided a patient interface for use with a respiratory support apparatus for delivering breathable gases to a patient, the patient interface comprising;

a. a cushion comprising:
   i. an internal cavity;
   ii. a face-contacting seal arranged to seal against the face of the patient;
   iii. opposed non-face contacting cushion side walls,
   iv. a dimension measured in a straight line between the cushion side walls directly beneath the nose and above the upper lip of the patient;
b. a gases inlet in fluid communication with the internal cavity;
c. a tether; wherein:
   the tether extends substantially laterally across the cushion inside the internal cavity between the cushion side walls, the tether being mounted to the cushion side walls, the tether being inextensible so as to resist the dimension increasing.

According to another aspect of this disclosure there is provided a patient interface for use with a respiratory support apparatus for delivering breathable gases to a patient, the patient interface comprising;

a. a flexible cushion comprising:
   i. an internal cavity;
   ii. a face-contacting seal arranged to seal against the face of the patient;
   iii. opposed non-face contacting cushion side walls;
b. a gases inlet in fluid communication with the internal cavity;
c. a tether,
   the tether extending substantially laterally across the cushion inside the internal cavity between the cushion side walls, the tether being mounted to the cushion side walls; wherein:
   the tether is further mounted to a further part of the cushion intermediate the cushion side walls such that the tether comprises a pair of secondary tether portions each extending between a respective cushion side wall and the further part of the cushion, and each configured to resist movement of one cushion side wall independently of the other cushion side wall.

The tether may be mounted so as to be spaced from the face of the patient.

According to another aspect of this disclosure there is provided a patient interface for use with a respiratory support apparatus for delivering breathable gases to a patient, the patient interface comprising;

a. a cushion at least partially defining an internal cavity, and comprising a proximal portion and a distal portion, the cushion comprising a pair of opposing cushion side walls, the proximal portion comprising a sealing flange arranged to seal against the face of the patient;
b. the distal portion comprising a gases inlet in fluid communication with the internal cavity;
c. a tether;
d. wherein the tether extends substantially laterally across the cushion inside the internal cavity between the pair of opposing cushion side walls, the tether being secured to the cushion side walls;
e. the tether being spaced from the proximal portion of the cushion;
f. the tether being inextensible.

According to one aspect of this disclosure there is provided a patient interface comprising a cushion having side walls, and a tether configured to extend between and be secured to the side walls, wherein the tether comprises a central portion between two tether side portions, the central portion being configured to be mounted to a central mount of the cushion.

According to one aspect of this the disclosure there is provided a patient interface comprising a cushion having side walls, and a tether configured to extend between and be secured to the side walls, and comprising opposed ends which extend through respective apertures in the side walls, wherein each end of the tether comprises a restraining component configured to resist the opposed ends being pulled through the respective apertures, under tensile load applied to the tether.

The tether may be integral with the cushion, or the tether and cushion may be separate components.

The patient interface may comprise a pair of laterally spaced mounts on the cushion, the tether being secured to the cushion by the laterally spaced apart mounts.

The cushion side walls may be laterally spaced by a predetermined distance, the tether being configured to substantially maintain the predetermined distance.

The tether may be configured to resist laterally outward movement of the cushion side walls. The tether may be configured to allow laterally inward movement of the cushion side walls.

The tether may be substantially inextensible under tensile forces. Such tensile forces may have at least a force component applied along the longitudinal axis of the tether in a direction towards the cushion side walls.

The tether may be collapsible under compressive forces. Such compressive forces may have at least a force component applied along the longitudinal axis of the tether in a direction away from the cushion side walls.

The tether may be inelastic.

The tether and the cushion side walls may be configured such that the tether is spaced from the face of the patient, when the patient interface is mounted on the patient.

The cushion may comprise a transition portion between each cushion side wall and the sealing flange, the tether being secured to the transition portion.

The tether and the cushion side walls may be configured such that the tether extends across, but is spaced from, the upper lip region of the patient.

The cushion may comprise a nasal bridge region, wherein the tether is positioned below the nasal bridge region.

The cushion may comprise a pair of side of nose portions, wherein the tether is positioned below the side of nose portions.

The side of nose portions may be provided on, or comprise part of, the cushion side walls.

The tether may comprise any one or more of:

a. a filament;
b. a wire;
c. one or more fibres;
d. a ribbon;
e. string;
f. a braided element.

The tether may be formed from any one or more of:

a. plastic;
b. metal;
c. silicone;
d. a woven material;
e. a knitted material
f. a braided material.

The tether may have:

a. a circular or elliptical transverse cross section.
b. a non-circular transverse cross section.
c. a polygonal transverse cross section.
d. a triangular transverse cross section.
e. a quadrilateral transverse cross section.
f. a square transverse cross section.

The tether may comprise a ribbon of oblong transverse cross section defined by two opposed longer faces, and two opposed shorter faces. The ribbon may be orientated such that one of the longer faces is adjacent the face of the patient. The ribbon may have a transverse cross section of between 0.2 and 0.8 mm by between 2.0 and 10.0 mm, preferably between 0.3 and 0.7 mm by between 3.0 and 8.0 mm, and in one example 0.4 by 5.0 mm.

The ribbon may:

a. comprise a recessed central portion configured to accommodate the patient's nose.
b. comprise end portions, the recessed central portion being narrower than the end portions.
c. be arcuate.
d. curve downwardly in use to define the recessed central portion.
e. curve forwardly, away from the patient's face.
f. curve through 180°
g. comprise one or more thickened portions.
h. comprise one or more thinned portions.
i. be configured such that the central portion of the ribbon is thinner than the remainder of the ribbon.
j. be configured such that the cross section of the ribbon varies along its length.

The tether may be twisted along its length. The tether may comprise a central portion between two tether side portions, the central portion being twisted relative to the two side portions. The central portion may be twisted so that a surface of the central portion is aligned with an adjacent interior surface of the cushion. The surface of the central portion of the tether, and the adjacent interior surface of the cushion may be substantially planar, the planar surfaces being substantially parallel.

The tether may comprise a central portion between two tether side portions, the central portion being configured to be mounted to a central mount of the cushion. Each tether side portion may extend across the cushion from a respective lateral mount to the central mount, such that each tether side portion can move independently of the other.

The central portion may be rigid.

The central portion may be arcuate.

The central portion may comprise one of a lug and a slot, the central mount of the cushion comprising the other of the lug and the slot, the lug being configured to be received in the slot to mount the central portion of the tether to the cushion. The lug may be received in and projects through the slot. The slot may be provided on the tether. The slot may be elongate. The slot may be elliptical.

The tether may comprise a front tether portion, the tether central portion being mounted to the cushion via the front tether portion which extends from the central portion to a front wall of the cushion. The front tether portion may be flexible.

The front and/or side tether portions may be secured to the central portion by any one or more of:

a. Knots.
b. Adhesive.
c. Overmoulding.
d. Welding.

The central portion of the tether may comprise a widened support region which engages the central mount of the cushion.

The central mount may engage the tether at an upper lip contacting region of the cushion.

The tether may be of non-uniform thickness, and/or shape, and/or transverse cross section, along its length. The tether may comprise at least one thinned region, the thinned region having a thinner transverse cross section than an adjacent region of the tether. The tether may comprise a plurality of thinned regions. The thinned regions may be equispaced along the length of the tether. The tether may comprise between two and ten thinned regions, preferably between three and eight, and in some examples five or six thinned regions. The tether may comprise the same number of thinned regions in each portion of the tether that extends between the central mount and respective lateral mounts. The or each thinned region may comprise a living hinge. The or each thinned region may have a thickness that is between 25 and 75% of the thickness of the tether, preferably between 35 and 65%, and in some examples is about 50%.

The may comprise a central portion between two opposed side portions, the two side portions having a larger thickness and/or transverse cross sectional area than that of the central portion.

Each laterally spaced mount may comprise a respective aperture in the cushion, the tether comprising opposed ends, each opposed end projecting through a respective aperture.

Each end of the tether may comprise a restraining component configured to resist the opposed ends of the tether being pulled through the respective apertures, under tensile load applied to the tether. Each restraining component may comprise a side support, secured to the tether, and configured to extend over at least a portion of a respective side wall of the cushion. Each side support may be elongate, having a longitudinal axis which is not aligned with the longitudinal axis of the tether. Each side support may be elongate, having a longitudinal axis which is inclined to the longitudinal axis of the tether, when the patient interface is viewed from the front. Preferably, respective upper portions of each said side support are spaced closer together than respective lower portions of said side support.

The longitudinal axis of each side support may extend along the cushion side wall, for example in a substantially vertical orientation when viewed along the tether longitudinal axis. Each side support may extend downwardly from an upper portion of the cushion. Each side support may extend from a position at or adjacent a top margin of the cushion. Each side support may extend substantially above and below the longitudinal axis of the tether. Each side support may comprise an enlarged portion configured to transfer load from the tether to the side support. The enlarged portion of each side support may be substantially planar, or may comprise at least a substantially planar portion, such that load transferred from the tether to the side supports is distributed across the cushion side walls.

Each side support may be arcuate, or may comprise at least an arcuate portion.

Each side support comprise a shape, and/or profile that conforms to the shape and/or profile of the region of the cushion side walls on which the side supports are located. For example, the side support may comprise one or more curved portions that substantially match one or more curved portions of the region of the cushion side wall on which the side support is mounted. An outer surface of each side support may be flush with an outer surface of the region of the cushion side walls on which the side supports are located. Each cushion side wall may comprise a recess configured to receive and locate a respective side support. When so received the side support may be configured so as not to project beyond an outer surface of the cushion.

Each side support may be more rigid than the cushion. For example, each side support could comprise a more rigid material or materials than the cushion, or may be structurally more rigid, for example by being thicker, or comprising one or more reinforced regions.

Each side support may comprise a mounting post, each mounting post extending through a respective aperture in the cushion side wall. The mounting post may extend sufficiently through the aperture so as to project into the interior of the cushion.

Each mounting post may comprise an enlarged portion, the enlarged portion engaging an interior surface of the cushion side walls to resist removal of the mounting post from the cushion. Each mounting post may terminate in the enlarged portion. The enlarged portion may be oblong, when viewed along a longitudinal axis of the mounting post.

The part of each mounting post that extends through the aperture in the cushion may be of substantially constant cross section.

The part of each mounting post that extends through the aperture in the cushion may be of varying cross section.

The cross section of the part of each mounting post that extends through the aperture in the cushion may increase as it extends into the cushion.

The mounting post may comprise an outer end having a relatively small cross section, and an inner end having a relatively large cross section, wherein the inner end comprises the enlarged portion of the mounting post.

The enlarged portion may be flush with the inner surface of the cushion.

The tether may be adjustably mounted on the cushion. The tether may be adjustably mounted on the cushion such that a lateral distance between the cushion side walls can be adjusted, the tether resisting an increase of the lateral distance. The lateral distance extends laterally across the patient interface, when the patient interface is viewed from the front.

The tether may comprise a central portion between opposed tether side portions, each side portion comprising a plurality of engagement formations which can selectively engage the cushion side walls. The lateral space between the lateral mounts may be adjusted by selectively engaging one of the engagement formations with a respective cushion side wall. The engagement formations may be spaced along the longitudinal axis of the tether. Each engagement formation may comprise a projection, preferably a rib or bead.

The tether may comprise a primary tether comprising a central portion and opposed tether side portions, the opposed side portions being secured to respective cushion side walls. The tether may comprise a secondary tether, extending away from the primary tether, and configured to engage a further part of the cushion. The secondary tether may be substantially straight. The patient interface may comprise a plurality of secondary tethers, each secondary tether extending between the primary tether and a respective further part of the cushion.

The primary tether may be substantially straight such that the central and opposed tether side portions are aligned along a longitudinal axis, the secondary tether extending radially outwardly from the longitudinal axis.

The primary tether may comprise two substantially straight portions, each extending between the central portion and a respective opposed tether side portion, the two substantially straight portions being inclined relative to one another. The angle between the two substantially straight portions, and the angle between each straight portion and the secondary tether, may be substantially equal.

The secondary tether may extend between the primary tether and a front portion of the cushion, the front portion being spaced from the patient.

The patient interface may comprise a plurality of tether side portions at each end of the central portion, each of the plurality of tether side portions being secured to the side walls of the cushion.

At least one of the tether side portions at each end of the central portion may extend substantially above, and at least one of the tether side portions at each end of the central portion may extend substantially below, the longitudinal axis of the central portion of the tether.

The tether may comprise two tether side portions; and a hinge positioned between the two tether side portions and configured such that the hinge enables the tether side portions to move towards one another under compression forces applied to the cushion.

The tether side portions may be substantially rigid.

The patient interface may comprise a plurality of hinges. In some embodiments, the patient interface may comprise two or three hinges.

The hinges may be configured such that, when compression forces are applied to the cushion, the tether side portions can move towards each other in a linear motion.

The hinges may be configured such that, when compression forces are applied to the cushion, the tether side portions can move towards each other without rotation of the tether side portions.

The flexible cushion may comprise headgear connectors, configured to connect the cushion to headgear.

The patient interface may comprise a frame, wherein the flexible cushion is mounted to the frame, the frame comprising headgear connectors to connect the frame to headgear.

The patient interface may comprise headgear configured to mount the patient interface on the patient's head.

The patient interface may comprise:

a. a full face cushion configured to extend around the nose and mouth of the patient.

b. a nasal cushion configured to extend around the nose of the patient.

c. an oral cushion configured to extend around the mouth of the patient.

d. an undernose cushion configured to have a portion which extends under the nose of the patient and contacts the patient's upper lip region.

The cushion may be collapsible.

According to an aspect of this disclosure there is provided a respiratory support apparatus comprising:

a. a flow generator configured to generate a flow of breathable gases;

b. the patient interface of any one of the preceding paragraphs.

The respiratory support apparatus may comprise any one or more of:

a. a humidifier;

b. a gas delivery conduit. The gas delivery conduit may be heated.

c. a controller.

Further aspects of the disclosure, which should be considered in all its novel aspects, will become apparent from the following description.

DESCRIPTION OF THE DRAWINGS

A number of embodiments of the disclosure will now be described by way of example with reference to the drawings in which:

FIG. 1*c* is a schematic front view of the cushion of FIG. 1*b* showing typical deformation of the cushion when subject to pressure from a gases flow into the patient interface, the dotted line indicating an example typical deformation of the cushion.

FIG. 2*a* is a front view of a patient interface in use where the patient interface comprises a rigid frame; and FIG. 2*b* is a front view of a patient interface in use where the patient interface does not have a rigid frame, showing example typical deformation of the cushion;

FIGS. 10*a* and 10*b* are perspective and front views of another embodiment of a tether and side supports in accordance with this disclosure, where the tether comprises a ribbon.

FIG. 11 is a part sectional view of the interior of a patient interface comprising the tether and side supports of FIG. 10.

DETAILED DESCRIPTION OF SPECIFIC EMBODIMENTS

Figure 1A:
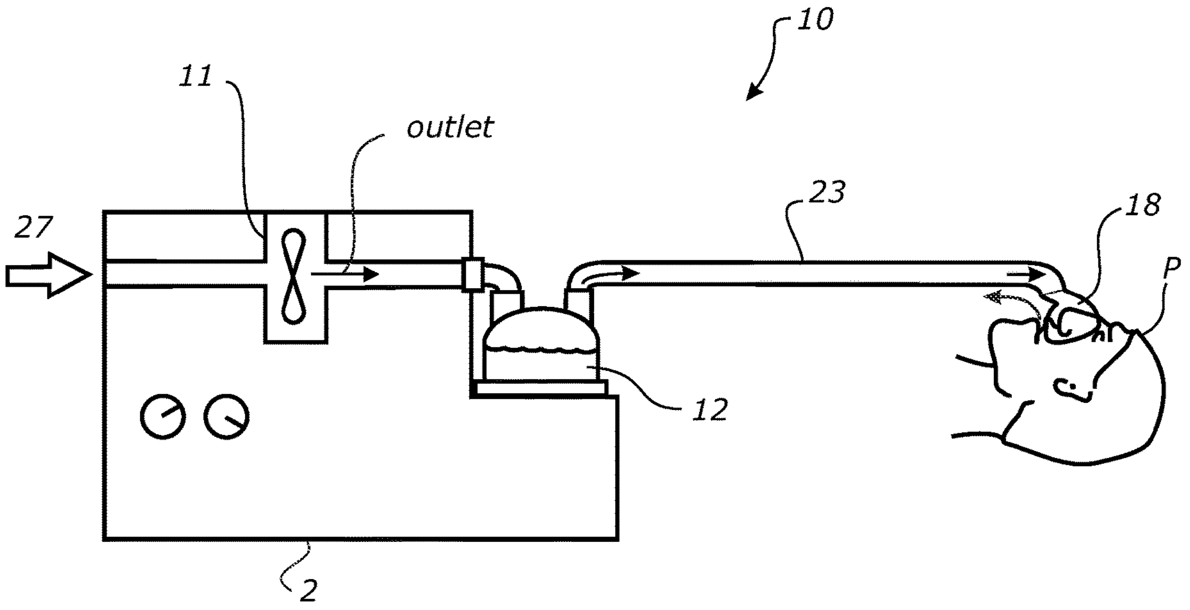
FIG. 1*a* is a schematic view of a respiratory therapy apparatus, comprising a patient interface.

FIG. 1 shows a schematic view of one type of known respiratory support apparatus 10 for delivering humidified and heated gases to a patient. The apparatus 10 comprises a housing containing a flow generator in the form of a blower unit 11, and a humidifier unit 12. In operation, atmospheric air 27 is drawn into the blower unit 11. The blower unit 11 generates a pressurized air or gases stream which is delivered to the inlet of a humidification chamber of the humidifier unit 12. The humidification chamber comprises water and is heated by a heater pad or plate. The humidified and heated gases stream exits the humidification chamber via an outlet of the humidification chamber and is delivered to the patient or user P via an inspiratory conduit or conduits comprising a flexible hose or gases conduit 23 and patient interface 18 as shown. The blower unit 11 and humidification unit 12 are typically connected via a series of connectors and/or conduits to allow gases to pass from the blower unit 11 to the humidifier unit 12.

The patient interface 18 shown in FIG. 1 is a nasal mask, covering the nose of the user P. However, it should be noted that in apparatus of these types, a mask that covers the mouth and nose, a full face mask, or any other suitable patient interface could be substituted for the nasal mask shown. A mouth-only interface or oral mask could also be used. The current disclosure relates to any patient interface that comprises a cushion that seals against the face of the patient, where the cushion can deform.

The humidification chamber typically comprises a rigid plastic receptacle or container that can be filled with a volume of water. In one known form, the base of the humidification chamber comprises a circular thermally conductive metal heater plate that is fixed within a complementary aperture provided in the base of the humidification chamber via, for example, overmolding of the plastic base about the peripheral edge of the heater plate. The overmolding forms a seal at the interface between the perimeter edge of the heater plate and surrounding plastic base surface of the chamber. In use, the heater plate contacts a heater pad or heater base upon which the humidification chamber rests and heats the volume of water in the chamber via conduction.

The patient interface 18, in a pressurised support apparatus, is a sealed interface that forms a seal with the patient P. The patient interface 18 comprises a cushion 100 having opposed cushion side walls 102. The cushion 100 comprises a gas inlet 104 to receive a gases flow from the apparatus 10 as described above. The gas inlet 104 may be provided on the front of the cushion 100, or in the example of FIGS. 1*b* and 1*c*, in the base of the cushion 100. The rear of the cushion 100 comprises a larger opening that at least partially receives the nose and/or mouth of the patient. The larger opening is defined by a cushion margin in the form of a seal 106 which seals against the patient's face. The seal 106 may comprise a sealing lip or flange, and may be of a thinner and/or more flexible construction than the remainder of the cushion 100. The seal 106 comprises a face contacting portion of the seal 106, with the cushion side walls 102 being non-face contacting portions. The above features of the cushion 100 define an internal gases cavity 108 of the cushion 100, that receives the gases flow from the apparatus 10. The seal 106 is typically integral with the cushion 100, but could be a separate component mounted to the cushion 100.

In accordance with this disclosure the cushion 100 is flexible so as to be relatively soft and deformable. These properties may be achieved via a combination of construction and material choices. Typically, the cushion 100 will be of a silicone material, with the thickness of the material optionally being varied in different regions of the cushion 100.

It is desirable to be able to provide a cushion 100 which is relatively light and has relatively low visual intrusion both externally and from the point of view of the patient wearing the cushion 100. It is also desirable for the cushion to be relatively easily deformable so that the comfort, fit and seal of the cushion against the patient's face is maximised. Whilst the present disclosure is not so limited, it can also be desirable to avoid having a rigid frame on which the cushion is mounted, the frame having headgear connectors for connection to headgear. The provision of a frame can be disadvantageous in terms of the desirable characteristics of the cushion and seal described above.

Such patient interfaces are often used by patients when the patient is sleeping or is otherwise resting in bed or in a reclined position. When a patient lies on their side, when side sleeping, typically part of the patient interface rests on the bed, for example on a pillow. This can move or deform the patient interface causing discomfort, and/or reducing the effectiveness of the seal with the patient's face.

It can be another problem that the cushion of such patient interfaces deforms in use, under pressure of the gases flow into the internal cavity of the cushion. This can be particularly so under higher pressures or flow rates. Providing a rigid frame on which the cushion is mounted can help to minimise this, with the accompanying disadvantages as outlined above. There can be a conflict between providing a cushion that is as comfortable, effective at sealing, and usable by the patient as possible, against providing a cushion that can handle higher pressures and/or flow rates.

Figure 1B:
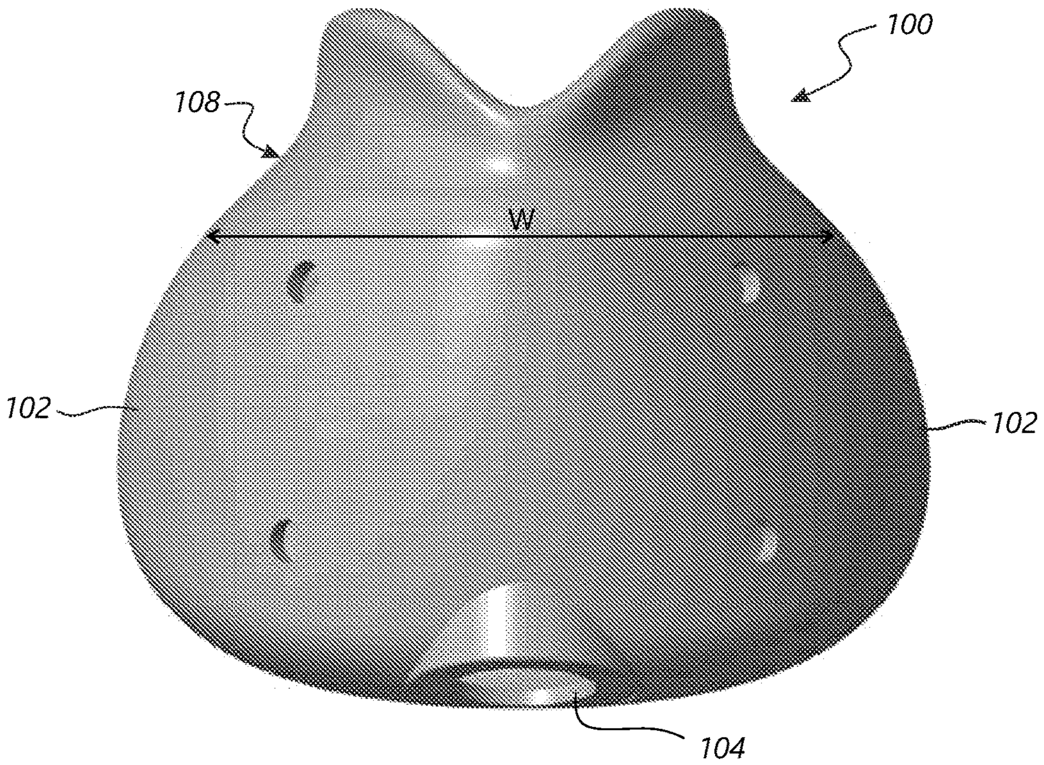
FIG. 1*b* is a front view of a cushion of a patient interface showing a lateral dimension W.

With reference to FIG. 1*b*, a cushion 100 of a patient interface comprises a laterally extending width dimension W, when the cushion 100 is in a rest condition. In the rest condition, the cushion 100 and cushion side walls 102 have not deformed. We have determined that it can be desirable to substantially maintain this dimension W, or at least to resist this dimension W increasing.

With reference to FIG. 1*c*, deformation of the cushion 100 typically results in the cushion walls, for example the side walls 102, expanding laterally outwardly in the direction of arrows A. This deformation causes the opposed lateral side walls 102 to move away from one another. Put another way, the laterally extending width dimension W, being the distance in a straight line between the cushion side walls inside the cavity 108, can increase. This deformation, or ballooning, of the cushion side walls 102 can reduce the effectiveness of the seal with the patient's face, causing undesirable leaks, because the geometry of the cushion 100, and in particular of the seal 106, changes.

Figure 2C:
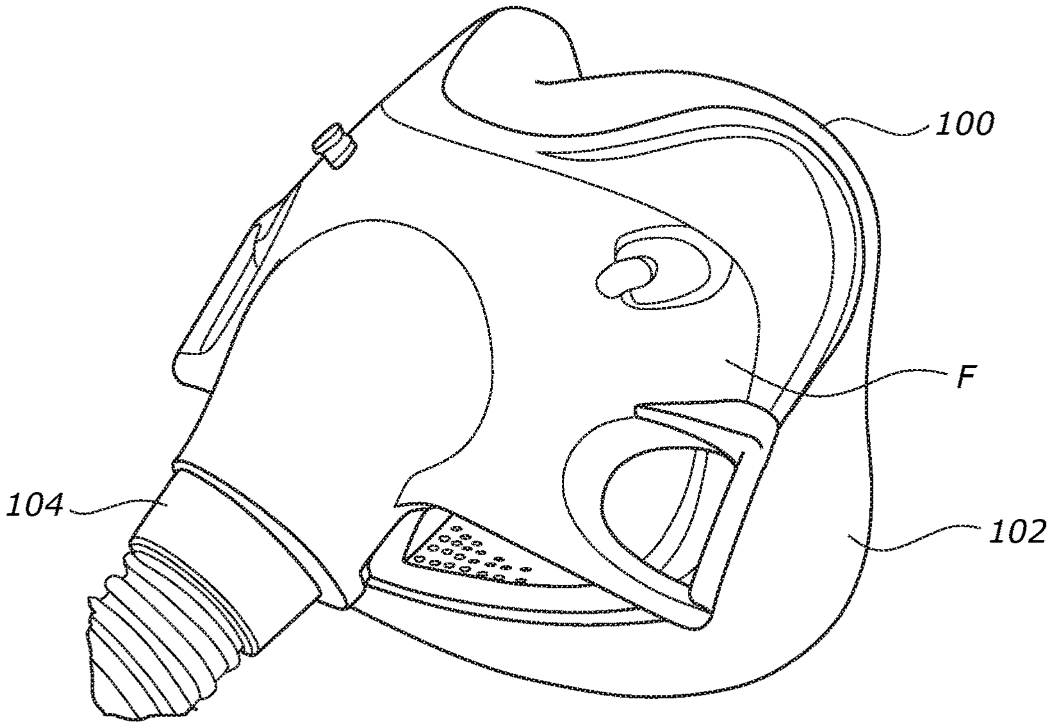
FIGS. 2*c* and 2*d* are perspective views of the patient interfaces of FIGS. 2*a* and 2*b* respectively.
Figure 2D:
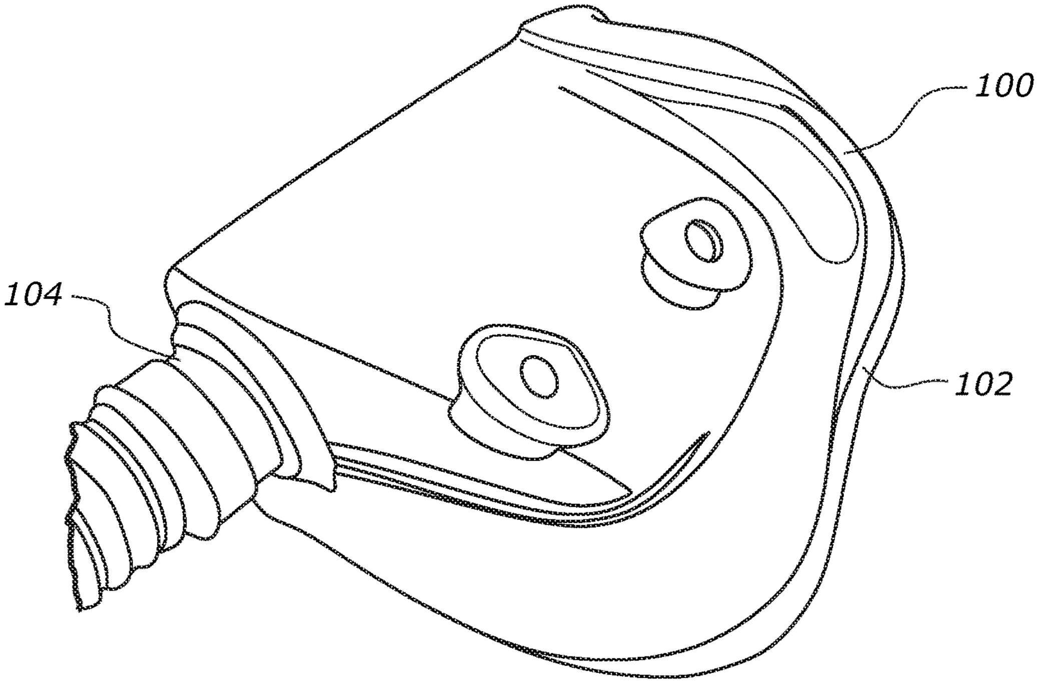

FIGS. 2*a* and 2*b* respectively show patient interfaces 18 including and omitting a rigid frame F respectively. It can be seen in FIG. 2*a* that the rigid frame F extends laterally across the cushion 100 and so will help to resist laterally outward movement of the cushion side walls 102. Nonetheless, there may still be some deformation of the cushion side walls 102. In FIG. 2*b*, the frame F is omitted, and deformation of the cushion side walls 102 may be more likely, and more significant, as illustrated by the ballooning indicated by arrows B. FIGS. 2*c* and 2*d* are perspective views of the patient interfaces of FIGS. 2*a*, 2*b* respectively, which show the frame F extending around the sides of the cushion 100, to some degree.

Figure 3:
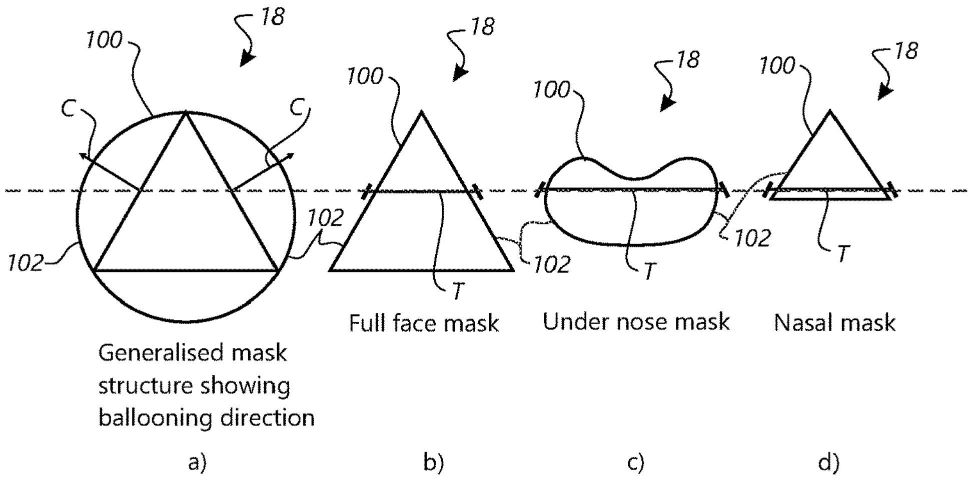
FIGS. 3*a* to 3*d* are schematic views from the front of different patient interfaces, with the patient interface of FIGS. 3*b* to 3*d* provided with a tether in accordance with this disclosure, with the position of the tether shown in dashed line.

With reference to FIGS. 3*a-d*, in accordance with this disclosure, we provide a patient interface 18 comprising a cushion 100 in which the cushion side walls 102 are connected by a tether T. FIG. 3*a* shows a patient interface without such a tether T, with typical example deformation of the cushion 100 being shown by arrows C. FIGS. 3*b* to 3*d* schematically show full face, under nose, and nasal patient interfaces, each comprising a cushion 100 and a tether T extending laterally across the cushion 100 and connecting the cushion side walls 102. The dashed line shows an example desirable position of the tether T in each interface. This desirable position is across and in front of the upper lip region of the patient, below the nose.

The tether T is configured to prevent or at least reduce any one or more of:

a. one cushion side wall 102A from moving laterally outwardly away from the other cushion side wall 102B.
b. the width dimension W between the opposed cushion side walls 102 from increasing.
c. ballooning of the cushion side walls 102.
d. the geometry of the cushion 102, and in particular the seal 106, from substantially changing.

Figure 4A:
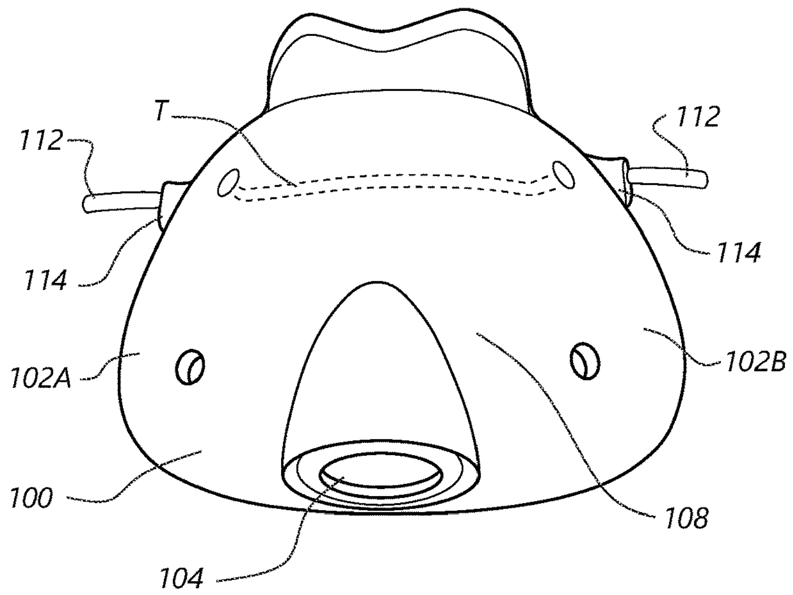
FIG. 4*a* is a front view of a cushion of an embodiment of a patient interface in accordance with this disclosure, comprising a tether extending between side walls of a cushion of the patient interface.
Figure 4B:
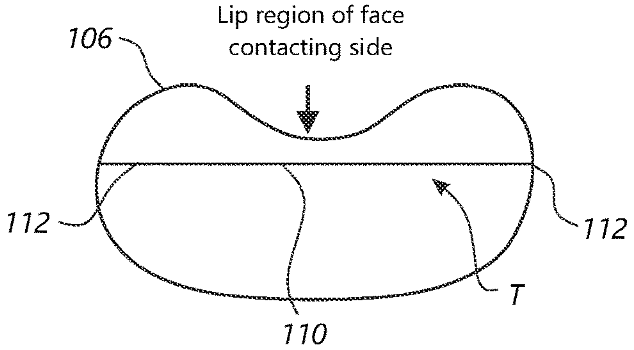
FIG. 4*b* is a schematic view of the cushion from above.

Referring to FIGS. 4*a-b*, the tether T in this example is flexible and non-rigid, but can resist tensile forces. The tether T collapses, that is, flexes or buckles, under compressive forces.

The tether T in this example is elongate, and comprises an elongate element in the form of a line or cord.

The tether T, as shown in FIG. 4*b*, extends laterally across the cushion cavity in an upper lip region of the patient, below the nose, but is spaced forwardly of the upper lip region so as to avoid contact with the patient's upper lip region.

The tether T comprises a central portion 110 which extends laterally across the cushion 100, inside the internal cavity 108. The central portion 110 is located so as to extend across, but avoid or at least reduce contact with, the upper lip of the patient, and below the nares of the patient. The tether T also comprises opposed side portions 112. These side portions 112 in this example pass through respective apertures in the cushion side walls 102 so as to project laterally outwardly from the cushion side walls 102. The side portions 112 are provided with lateral mounts which in this example comprise retainers 114 to secure the side portions 112 to the respective side wall 102, and are thus able to resist tensile forces typically associated with ballooning of the cushion 100 under pressure. The retainers 114 may comprise a knot of the side portions 112, or could comprise a clamp or other separate retaining element secured to each side portion 112.

Figure 5A:
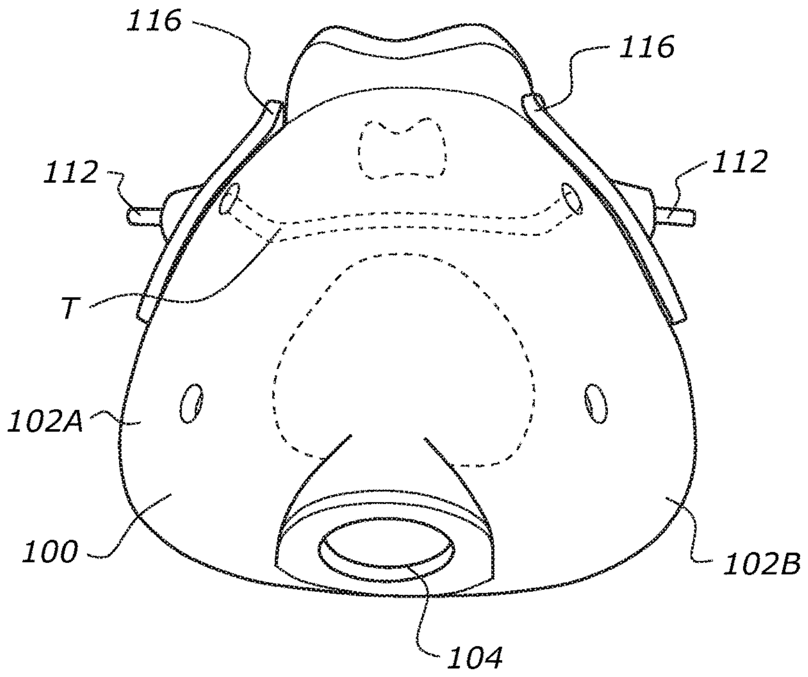
FIG. 5*a* is a front view of another embodiment of a patient interface in accordance with this disclosure, having side supports.
Figure 5B:
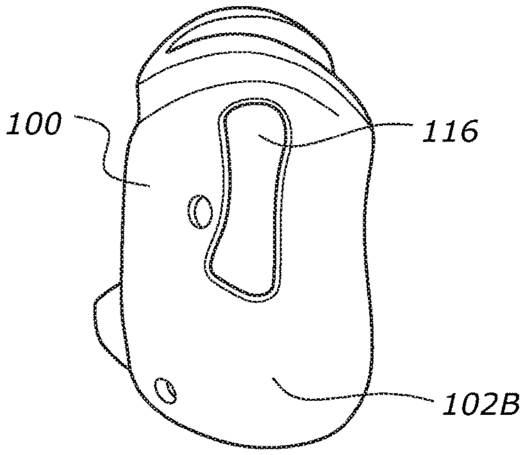
FIGS. 5*b* and 5*c* are side and plan views of the patient interface showing the side supports schematically.
Figure 5C:
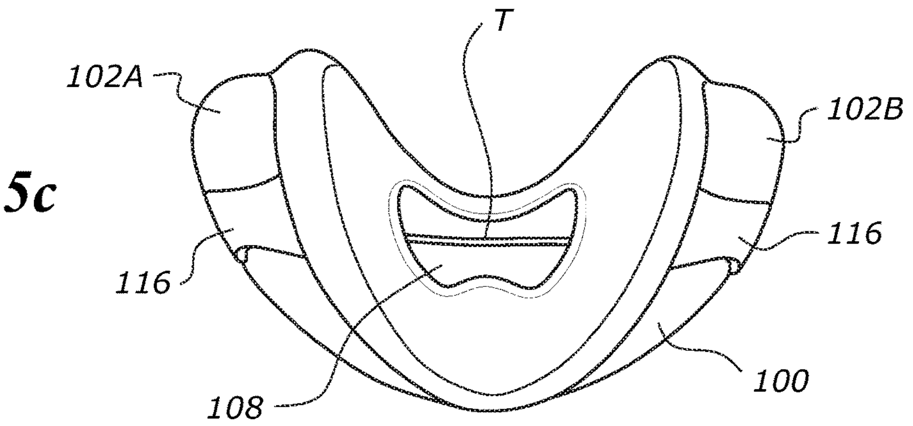

Referring to FIGS. 5*a-c*, the lateral mounts in this example comprise side supports 116 in the form of elongate elements that each rest against respective cushion side walls 102, on the outside of the cushion 100. The side supports 116 comprise apertures through which the tether side portions 112 extend, so that the side portions 112 are each secured to a respective side support 116. Each side support 116 has an area, when viewed from the side along the longitudinal axis of the tether T, that is relatively large, and considerably larger than the cross sectional area of the tether T, so as to distribute forces from the tether T across a relatively large area of the cushion side walls 102.

The side supports 116 in this embodiment are elongate when viewed from the side, and extend both vertically up each cushion side wall 102, above the tether longitudinal axis, and also vertically down each cushion side wall 102, below the tether longitudinal axis. The side supports 116 may be substantially oblong, or may be other elongate shapes, such as elliptical for example. The side supports 116 could be circular for example.

In the FIG. 5 embodiment the side supports 116 are substantially planar, being slightly arcuate when viewed from the front of the patient interface 18.

Referring now to FIGS. 6 to 9, the side supports 116 in this embodiment are arcuate. In this embodiment, the side supports comprise composite curved regions. In this embodiment, the side supports 116 are of a shape, and curvature, and profile that substantially match the shape and curvature and profile of the region of the cushion side walls 102 against which the side supports 116 engage.

In this embodiment, each cushion side wall 102 comprises a recess 120, each recess 120 being sized and shaped to receive a respective side support 116. The outer surface of each side support 116, when the side supports 116 are received in the recesses 120, is substantially flush with the outer surface of the cushion side walls 102. The outer surface of the side supports 116 does not substantially project beyond the outer surface of the cushion. The recesses 120 thus positively engage and locate the side supports 116. This configuration also improves the aesthetics of the patient interface 18. It has been determined that the aesthetics of a patient interface can surprisingly have a significant impact on patient compliance in successfully and reliably using the patient interface.

In the FIGS. 6 to 9 embodiment, the side supports 116 extend vertically up each cushion side wall 102 to support the region of the side wall 102 where ballooning of the cushion 100 typically occurs, or is particularly significant. The side supports 116 extend upward from the tether longitudinal axis, above the upper lip region, past the base of the user's nose, but preferably not so far as to affect the user's line of sight. The side supports 116 extend vertically down each cushion side wall 102 to distribute forces along the side of the cushion 100. The side supports 116 extend down below the user's upper lip, but preferably not below the user's mouth.

As with the FIG. 5 embodiment, the tether T extends substantially horizontally laterally across the cushion 100, in the front of lip area of the patient, avoiding contact with the patient's mouth and nose areas.

In this example the tether T is formed from a non-stretch inextensible material, such as nylon. This resists relatively high tensile forces along the tether T in a laterally outward direction, but provides relatively little resistance to compressive forces along the tether in a laterally inward direction. The tether T is preferably flexible in that if the tether T is held at one end only, the tether T will not support itself under its own weight.

The tether T could be configured to buckle when subject to typical compressive forces exerted on the tether T in use, for example, when the cushion is compressed during side sleeping. For example, the tether T could be sufficiently rigid not to bend, if held only at one end.

The tether T may be substantially inelastic.

Figure 6:
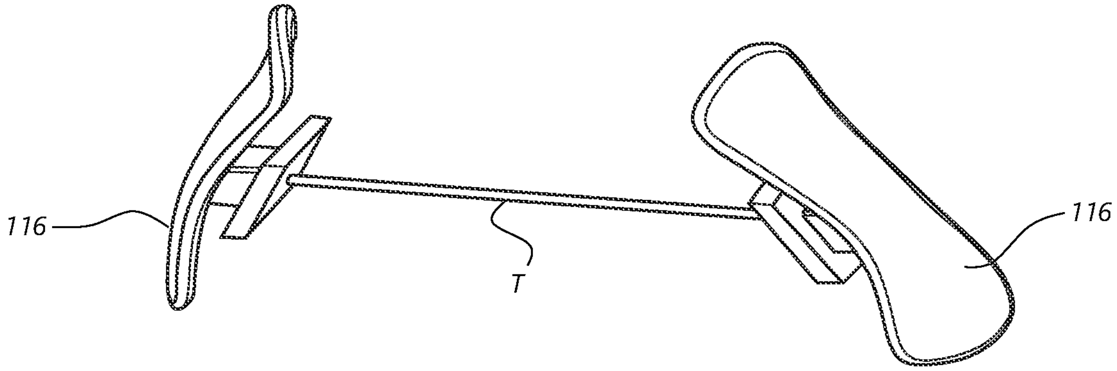
FIG. 6 is a perspective view of a tether and side supports of a patient interface in accordance with this disclosure.
Figure 7:
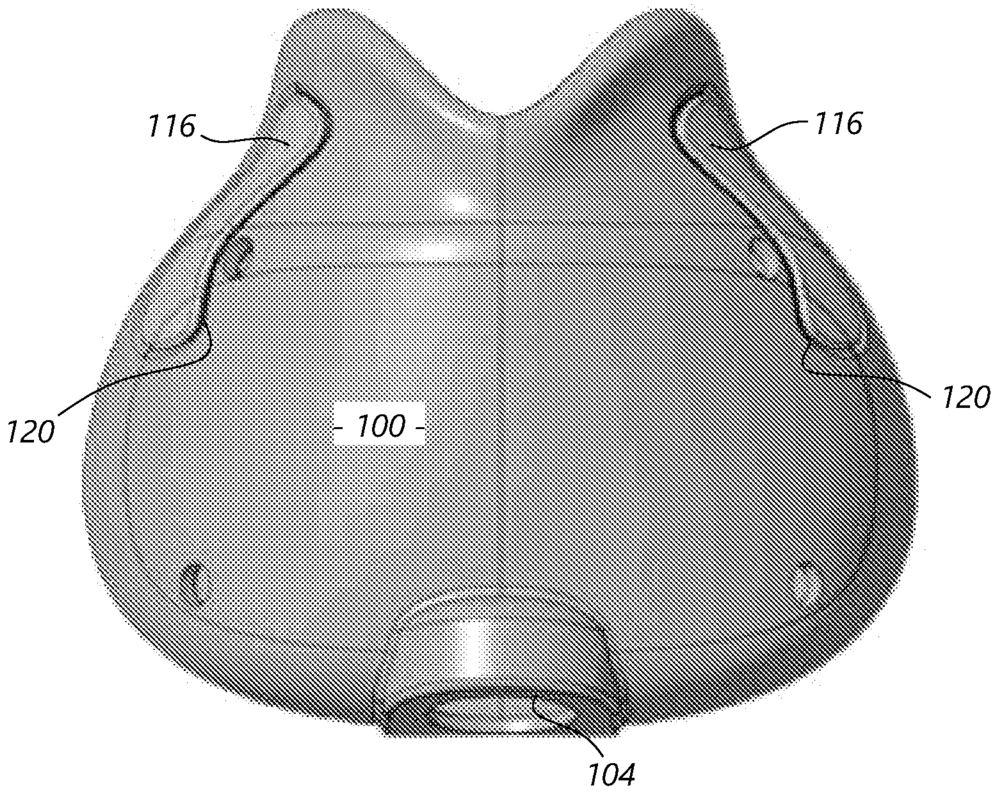
FIG. 7 is a front view of a patient interface comprising the tether and side supports of FIG. 6.
Figure 8:
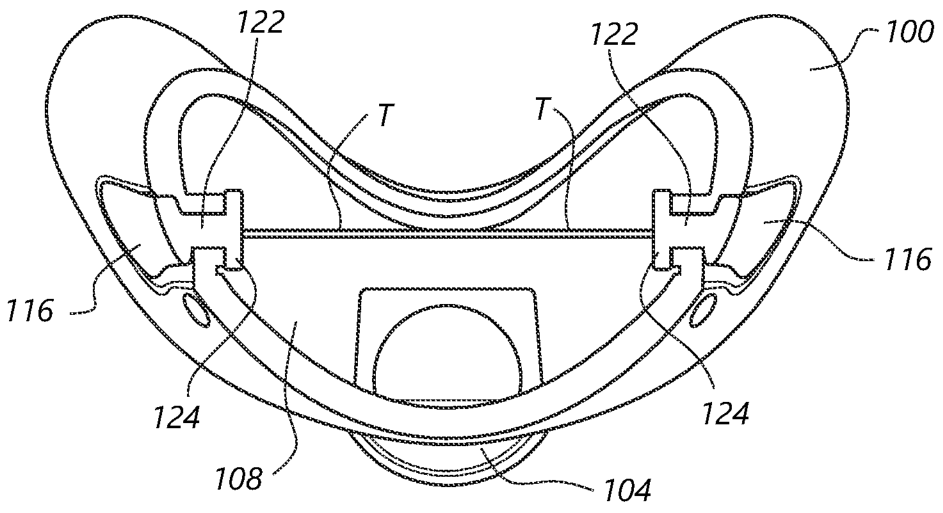
FIG. 8 is a part sectional plan view of the patient interface of FIG. 7.
Figure 9:
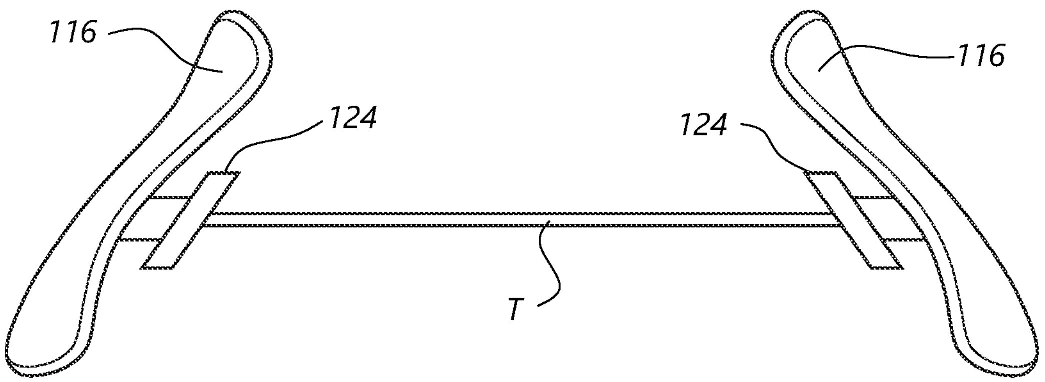
FIG. 9 is a front view of the tether and side supports of FIG. 6.
Figure 12C:
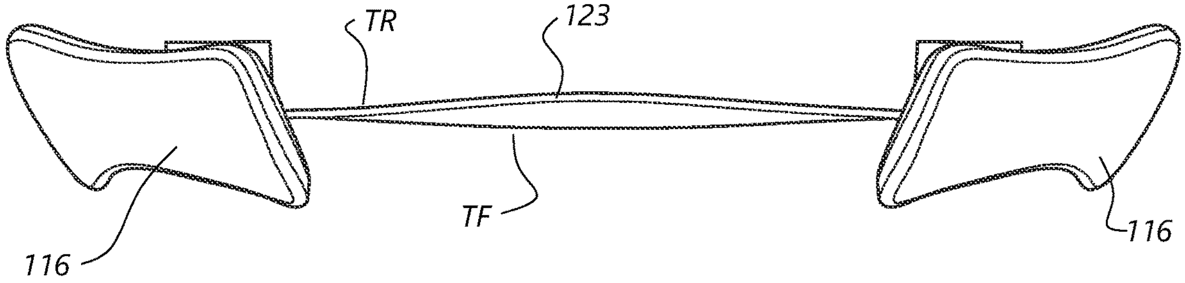
FIG. 12*a* is a perspective view of another embodiment of a tether and side supports in accordance with this disclosure, with FIG. 12*b* being a part sectional view of the interior of a patient interface comprising the tether and side supports, and FIGS. 12*c* and 12*d* being plan and front views respectively.
Figure 12D:
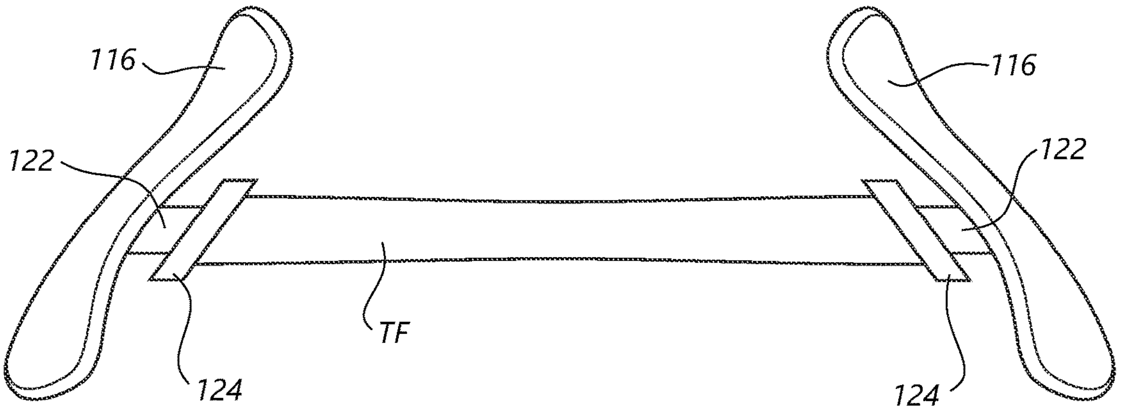

Referring to FIGS. 6, 8 and 9 in particular, the tether T and side supports 116 may be integral, so as to form a tether structure, separate from the cushion 100.

Each side support 116 may be secured to the tether T itself, via a respective mounting post 122. Each mounting post 122 extends through a respective aperture in the cushion side walls 102, the mounting posts 122 having substantially the same shape and diameter as the apertures. If the apertures and transverse cross section of the mounting posts 122 are non-circular, the engagement of the mounting posts 122 with the apertures can prevent twisting or rotation of the tether T. Each mounting post 122 comprises an enlarged region 124 that engages the interior surface of the cushion side walls 102 to securely locate the tether T against the interior surface of the cushion 100.

One benefit of the tether T of the above embodiments is to reduce transfer of load to the non-pillow side of the cushion 100 during side sleeping by reducing the likelihood of load transferring across the cushion 100 by rigid components as one side of the cushion 100 is compressed by the pillow. The side supports 116 can aid in maintaining the seal structure and shape under higher pressures, preventing, or at least minimising leakage caused by the upper seal region ballooning outwards.

In the embodiments of FIGS. 5 to 9, the tether T has a substantially uniform transverse cross section along its length. In these embodiments the transverse cross section of the tether T is substantially circular. However, other transverse cross sections may be provided, including non-circular, polygonal, triangular, quadrilateral, square or oblong for example.

Referring now to FIGS. 10 and 11, a further embodiment in accordance with this disclosure comprises a patient interface 18 and a tether T. The tether T comprises a front surface TF and rear surface TR when viewed along the longitudinal axis of the tether T, the rear surface TR being adjacent the upper lip region of the patient P, when the patient interface 18 is worn by the patient P. Tether T in this embodiment is shaped such that at least the rear surface TR is substantially flat, or comprises a relatively slight curve between the upper and lower margin of the tether T. Rear surface TR can thus distribute any potential contact force with the patient's upper lip, if the rear surface TR comes into contact with the patient during use.

As can be seen in FIGS. 10 and 11, the tether T comprises a ribbon. The ribbon has substantially flat front and rear surfaces TF, TR. In this embodiment the ribbon may be of oblong transverse cross section over a substantive part of its length, and in this embodiment across all of its length between the side supports 116. The ribbon, when viewed in transverse cross section comprises two opposed longer sides, being front and rear surfaces TF, TR, connected by two opposed shorter sides. The tether T in this example thus has a larger cross sectional area as compared to the circular cross section tether T of FIGS. 5 to 9. The tether T is oriented such that the longer sides are substantially vertical, and are substantially parallel to the upper lip region of the patient. This minimises the likelihood of contact with the patient's upper lip region. If there is such contact the substantially flat rear surface TR of the tether T can brush against the upper lip region without digging in or cutting the patient's face. The ribbon may, for example be about 0.4 mm by 5.0 mm in one example. Other cross sectional shapes of tether T, when viewed along the tether longitudinal axis, are envisaged, preferably shapes having a substantially flat surface or surface portion that contacts the cushion 100, to distribute load along the lip region. For example, the tether T could be elliptical or triangular.

Referring now to FIGS. 12*a-d*, a further embodiment in accordance with this disclosure comprises a patient interface 18 and a tether T. Tether T further comprises a central portion 123 which is twisted relative to the two opposed end portions. Tether T is twisted about the longitudinal axis of the tether T.

In this embodiment, the central portion 123 of the ribbon is twisted such that the longer side of the ribbon in the upper lip region of the patient is inclined toward the patient. This twisted central portion 123 is intended to be twisted sufficiently to be aligned with a lip band region 125 of the seal 108 of the cushion 100, such that if the ribbon contacts the lip band region 125, any load is distributed evenly so as to not be uncomfortable or painful for the patient.

Further, by providing support to the side wall 102 of the cushion 100, closer to the patient, less torque is applied by side loading when the patient is side sleeping. Such support is not associated with a typical mask frame that extends relatively far from the patient. Further, the support to side walls 102 is an independent support, which is less susceptible to external forces (e.g., hose pull).

Figure 13A:
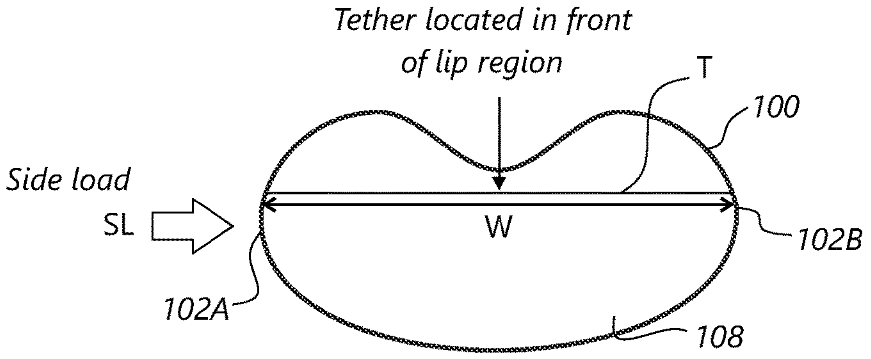
FIG. 13*a* is a schematic plan view of a cushion with a tether in accordance with this disclosure prior to application of a side load.
Figure 13B:
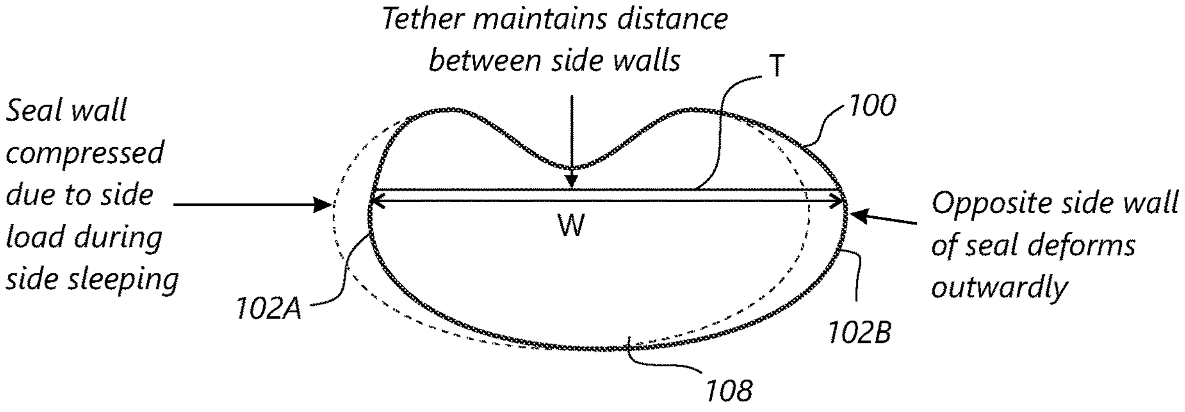
FIG. 13*b* is a plan view corresponding to FIG. 13*a* showing the deformation of the cushion under the application of the side load.
Figure 14A:
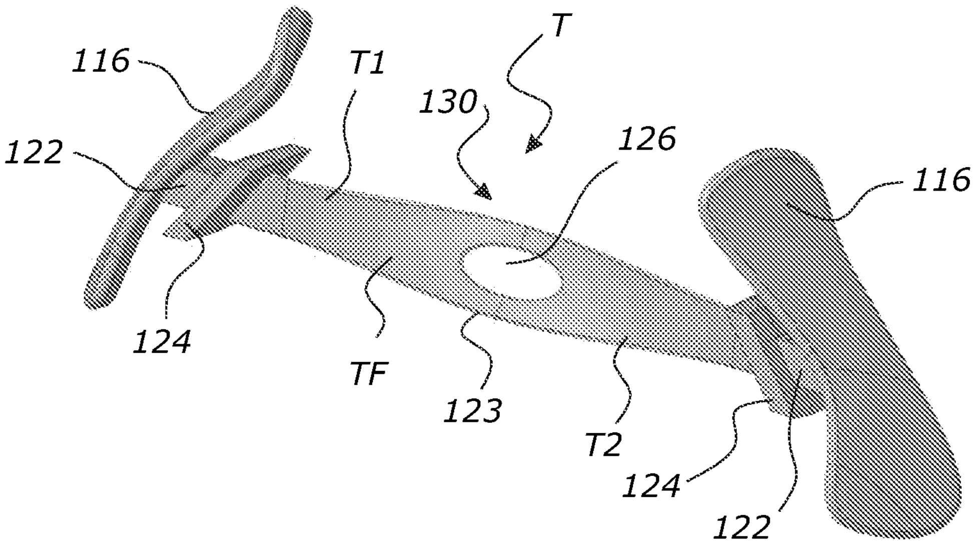
FIG. 14*a* is a perspective view of another embodiment of a tether and side supports in accordance with this disclosure, with FIG. 14*b* being a part sectional view of the interior of a patient interface comprising the tether and side supports, and FIGS. 14*c* and 14*d* being plan and front views.
Figure 14B:
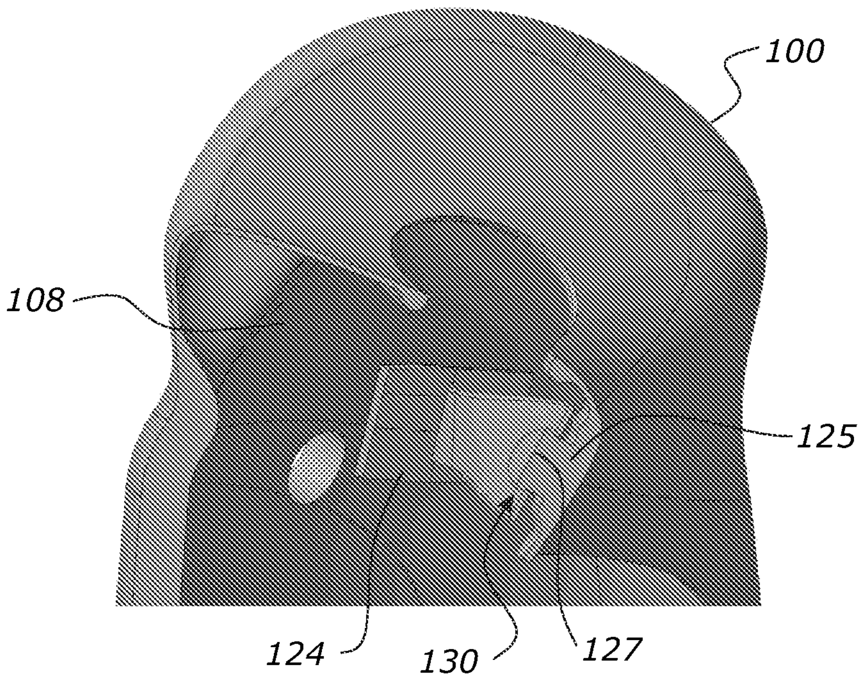
Figure 14C:
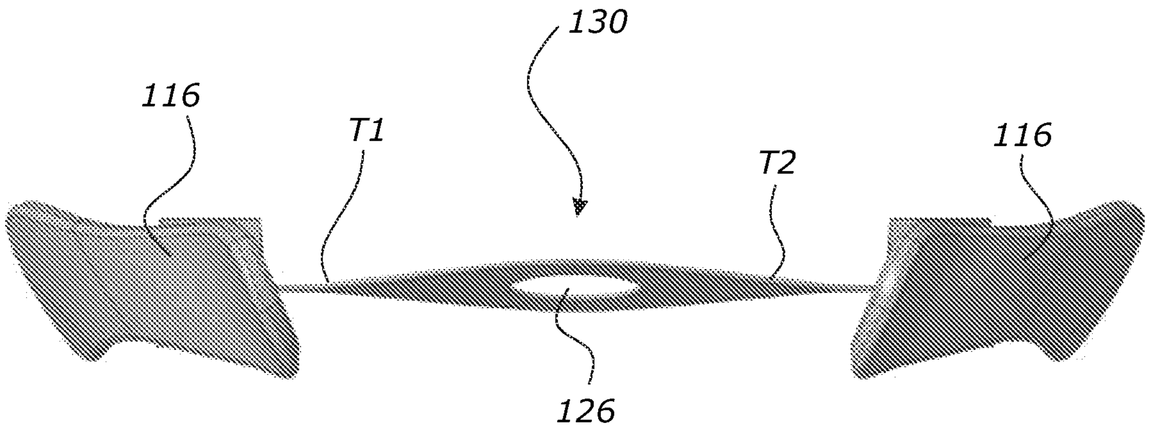
Figure 14D:
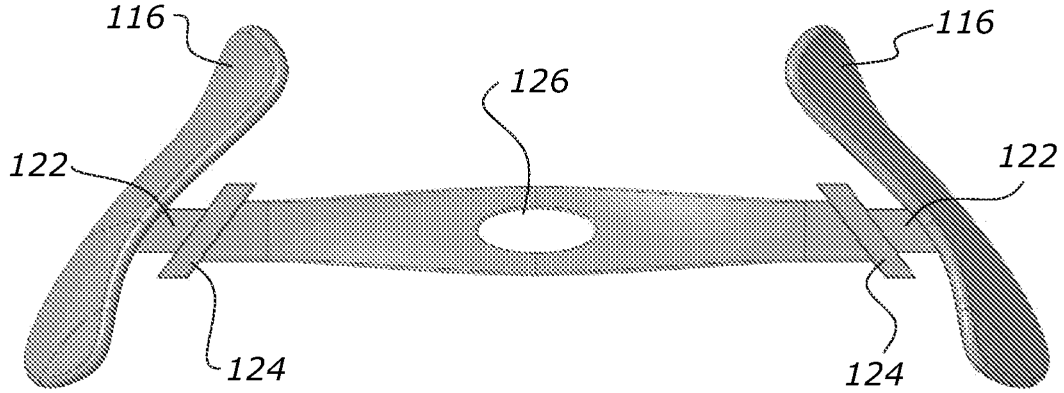

Referring to FIG. 13, the effect of a side load SL applied to the cushion 100, for example when a patient is side sleeping, is shown. The application of a side load force SL to a side wall 102 of the cushion 100 can be seen in FIG. 13*b* where one side wall 102A deforms inwardly. The opposite side wall 102B (the side wall 102 not resting on the pillow for example) deforms laterally outwardly. In that instance, tether T may serve to substantially maintain the laterally extending width dimension W, but can also allow some laterally outward deformation of the other cushion side wall 102. In other words, the overall width dimension W remains substantially constant, but both cushion side walls 102 deform in the same direction (to the right in FIG. 13*b*).

Referring now to FIGS. 14*a-d* a further embodiment in accordance with this disclosure comprises a patient interface 18 and tether T having a central tether mount connection 125 to mount a central part of the tether T to a central part of the cushion 100. This serves to effectively split the tether T into two tether side portions, T1 and T2, each of which can move independently of the other. Thus, if one cushion side wall 102 deforms, for example under a side loading force SL, the opposite cushion side wall 102 can remain undeformed. The earlier described tethers T could incorporate a central tether mount in order to achieve similar function.

An example embodiment of a tether T incorporating a central mount can be seen with reference to FIG. 14 where a tether T comprises a ribbon, and is twisted along a substantial part of its length.

In this example, the tether T is provided with an aperture 126 in the central portion of the tether T. The aperture 126 comprises part of the central tether mount connection 130, configured to secure the central portion of the tether T to a central portion of the lip band 125 of the cushion 100. The aperture 126 may be configured to receive a lug 127 on the cushion 100. This central mount 130 resists any movement of the central portion of the tether T relative to the cushion 100. The central tether mount 130 separates the tether T into two independent tether portions T1, T2, each tether portion T1, T2 extending between the central tether mount 130 and a respective cushion side wall 102.

Figure 16A:
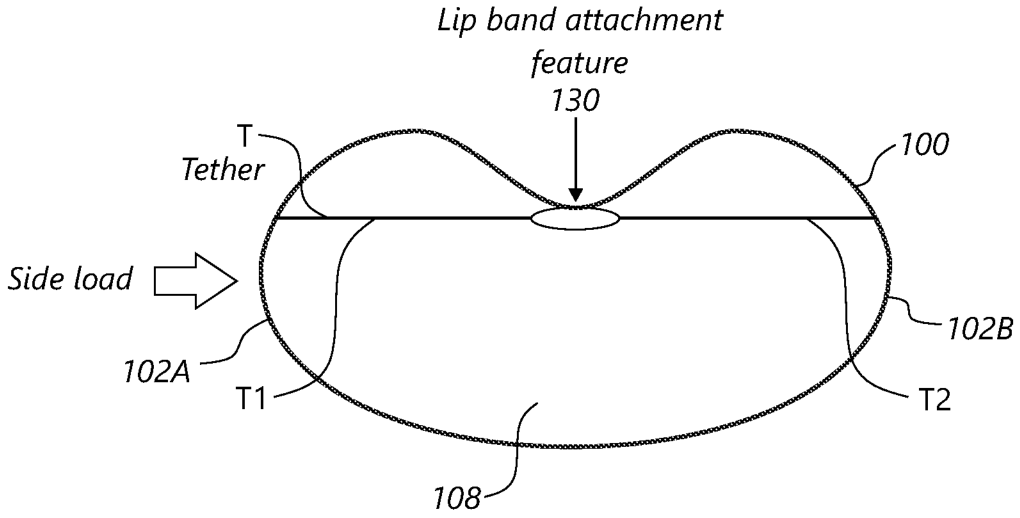
FIGS. 16*a* and 16*b* are schematic plan views of a patient interface in accordance with this disclosure, showing the patient interface in resting and deformed conditions respectively.
Figure 16B:
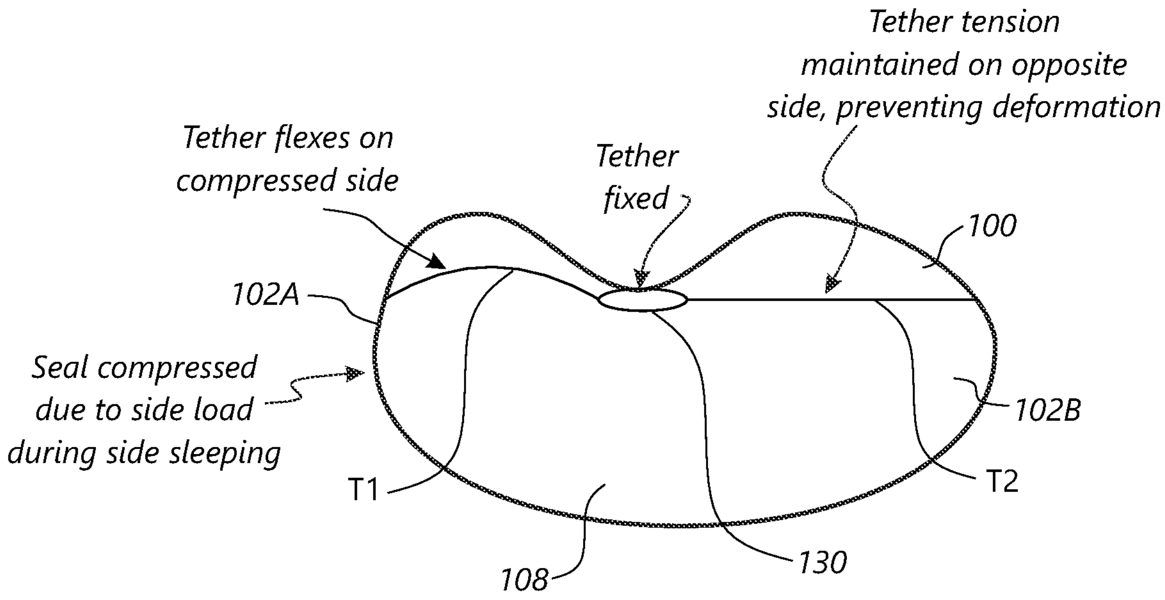

With additional reference to FIG. 16, providing two independent tether portions T1, T2, maintains the advantages stated above of preventing lateral expansion of the cushion side walls 102, and preventing the lateral width dimension W between the cushion side walls 102 from increasing. However, it also allows one side of the cushion 100 to collapse or be deformed, whilst continuing to prevent lateral expansion of the other side of the cushion, when the cushion 100 is under side load. Thus, if a patient is side sleeping, with the cushion 100 resting on the pillow, the side of the cushion in contact with the pillow can collapse, tether portion T1 having little resistance to compressive load. Because the other side of the cushion 100 has an independent tether portion T2, portion T2 can still resist any lateral deformation of that side of the cushion 100. Thus, at least one side of the cushion 100 still maintains its shape and geometry, and consequently maintains a seal with that side of the patient's face, even if the other side of the cushion 100 is significantly deformed. Consequently, mounting a central part of the tether to the cushion, provides a tether comprising two tether portions, each extending between the central mount and a respective cushion side wall 102, that operate independently. A compressive force applied to one tether portion is not transferred to the other tether portion. Compressive forces applied to one cushion side wall 102 therefore have no effect, or a reduced effect, on the other cushion side wall 102.

Referring now to FIG. 15, a further embodiment in accordance with this disclosure comprises a patient interface 18 and tether T. In this embodiment a plurality of living hinges 132 are provided spaced apart along the length of the tether T. These living hinges 132 are examples of regions of predetermined weakness along the length of the tether T, and allow the tether T to be generally thicker, with the regions of predetermined weakness improving the flexibility of the tether T, and reducing side load transfer. For example the tether T in this example could be around 0.8 mm thick, as compared to 0.4 mm for the examples above. The thickness of the living hinges 132 may be around half the thickness of the tether T, i.e. 0.4 mm in this example. Any number of living hinges 132 could be provided as required. It may be desirable to provide the same number of living hinges 132 for each tether portion T1, T2, for example 1, 2, 3, 4, or 5 living hinges. The living hinges 132 may be equispaced along the length of each tether portion T1, T2, or the spacing could be variable. The spacing, and number of, living hinges 132 may be selected to achieve the desired flexibility of the tether T. The living hinges 132 can be applied to any tether T in accordance with this disclosure. In the example of FIG. 15, the living hinges 132 are part of a tether T of ribbon structure, having a central mounting aperture 126.

Figure 17A:
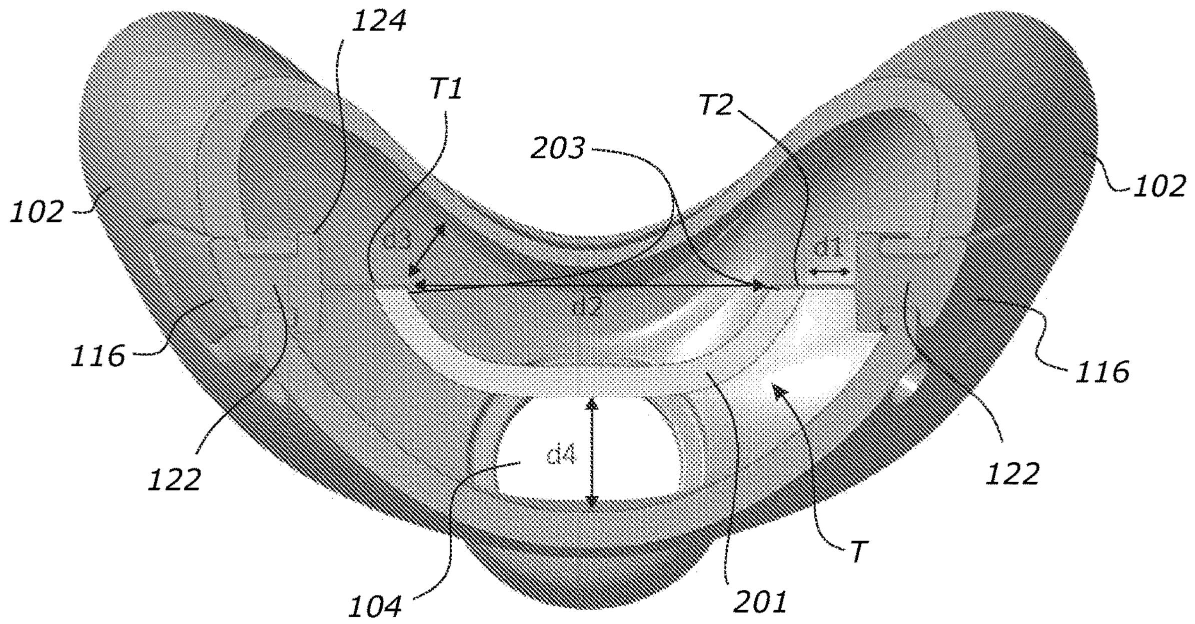
FIG. 17*a* is a part sectional plan view of another embodiment of a patient interface in accordance with this disclosure, comprising another tether.
Figure 17B:
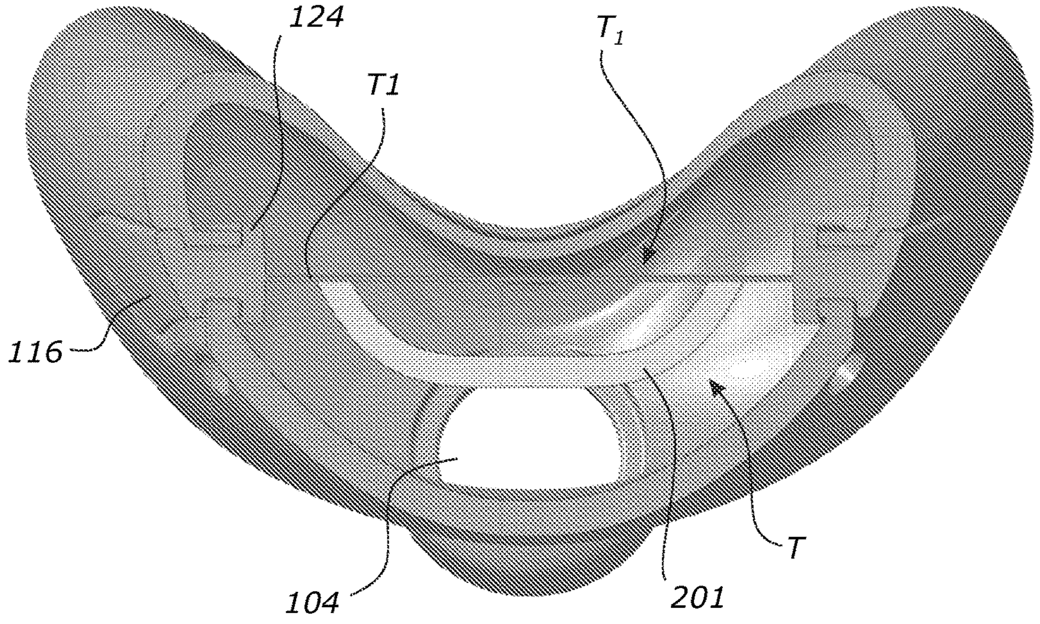
Figure 18A:
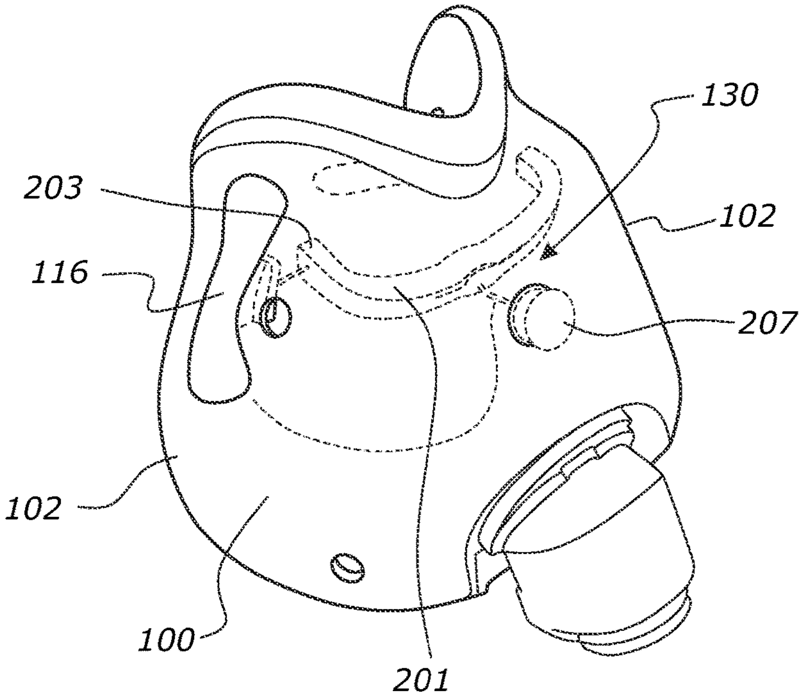
FIG. 18*a* is a perspective view of the patient interface of FIG. 17, where the tether is modified to include a central mount.

Referring now to FIGS. 17 and 18, embodiments of a patient interface 18 and tether T are disclosed in which the tether T comprises a rigid element, intermediate the side walls 102 of the cushion 100.

In the embodiment of FIG. 17, the independent tether portions T1 and T2 are interconnected by a rigid element 201. The tether portions T1 and T2 are relatively flexible and can bend so as to resist tensile forces but collapse under compression. The tether portions T1, T2, allow for a collapse mechanism with minimal resistance.

The rigid element 201 in this example is arcuate, having opposed ends 203 connected to the tether portions T1, T2. The ends 203 curve into a substantially straight central portion 205, such that the central portion 205 is proximal the front of the cushion 100 and distal the rear of the cushion 100 and seal 106.

The central portion 205 being spaced from the rear of the cushion 100 provides improved clearance between the tether T and the lip and nose of the user. The rigid element 201 is able to resist bending under tensile and/or compressive forces.

Figure 18B:
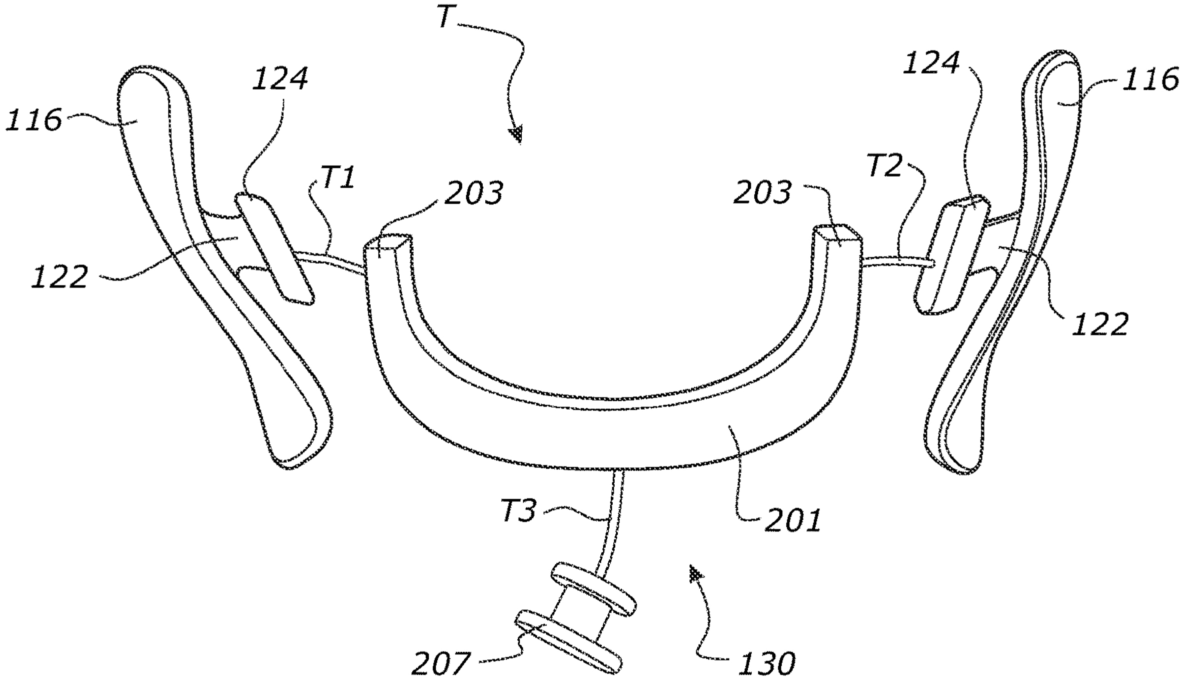
FIG. 18*b* is a plan view of the tether of FIG. 18*a*.

As can be seen in FIG. 18*b*, the tether portions T1 and T2 comprise flexible filaments, for example from braided polyethylene. The rigid element 201 may be of polypropylene.

FIG. 17*a* indicates various dimensions of this embodiment:

a. D1—The length of the flexible tether portions T1, T2, which provides buckling capacity.
b. D2—The width of the rigid element 201, which clears the lip of the patient.
c. D3—The distance between the rigid element 201 and the lip of the patient.
d. D4—The distance from the rigid element 201 to the front wall of the cushion 100.

The larger the dimensions D1 and D4, the more buckling capacity provided, as the sides and front of the cushion 100 are able to buckle a further distance under side loading for example. With constant cushion dimensions, it may be necessary to decrease dimensions D2 and D3 to increase dimensions D1 and D4. It is thus desirable to maximise D1 and D4 while keeping D2 and D3 sufficiently large to clear the patient's face, and in particular their nose and/or lip.

In the embodiment of FIG. 18, the rigid element 201 comprises a central tether mount connection 130, configured to secure the central portion of the tether T to a central part of the cushion 100. This central tether mount 130 resists movement of the central portion of the tether T relative to the cushion 100. The central tether mount 130 extends from the central portion 205 of the rigid element 201.

The rigid element 201 and central tether mount 130 may for example resist upward and/or downward movement of the tether T in a direction that may cause the tether T to contact the patient's face, for example their nose and/or lip.

The rigid element 201 and central tether mount 130 may for example resist lateral movement of the tether T when the cushion 100 is laterally deforming or buckling, for example when subject to side loading.

The central tether mount 130 may also comprise a flexible filament T3. The flexible filament T3 may be secured to the front of the cushion 100 via a suitable connector 207. Connector 207 comprises a narrower region 209 of reduced diameter, configured to be received in a corresponding aperture of the cushion 100, and a pair of opposed enlarged regions 211 that engage the inner and outer surfaces of the front wall of the cushion 100.

The connector 207 may be configured for connection to the cushion 100 in a position such that the rigid element 201 is angled downwardly when viewed from the side, to avoid contact with the nose of the patient, but not so far as to contact the upper lip.

Figure 18C:
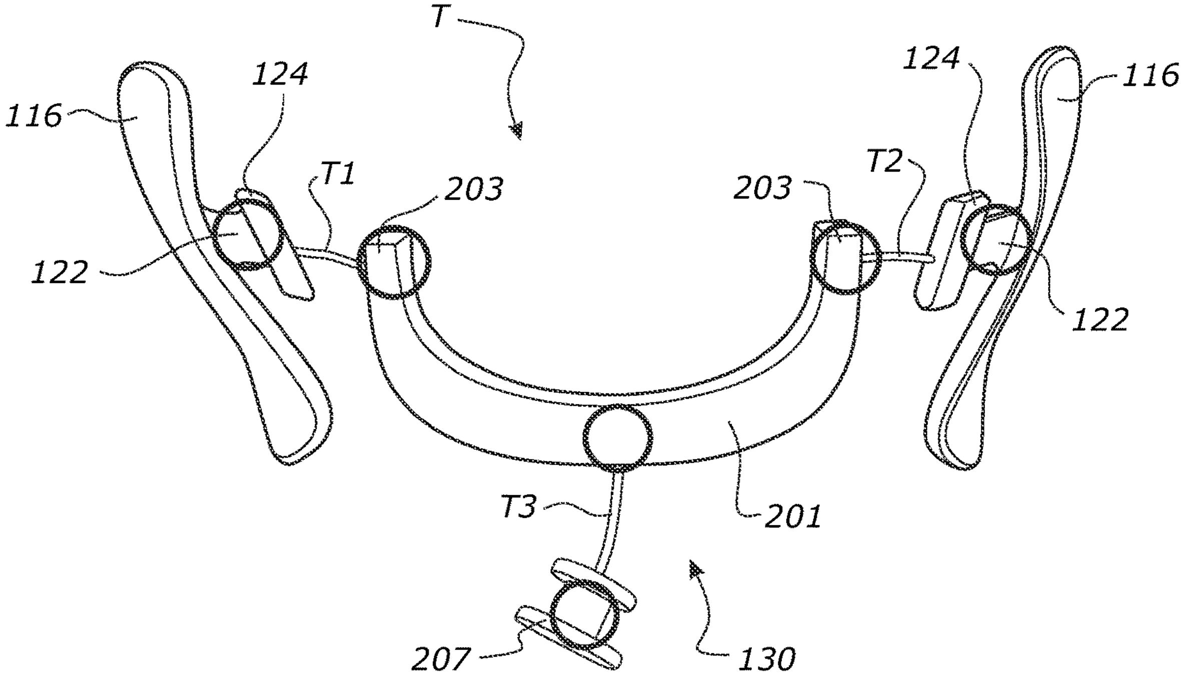
FIG. 18*c* is a plan view of the tether of FIG. 18*a* showing connections between different parts of the tether.

As can be seen in FIG. 18*c*, each filament (of tether portions T1, T2 and filament T3 of the central tether mount 130) may be connected to the remaining parts of the tether T using knots, for example at each of the circled regions shown. Alternatively the filaments T1, T2, T3 may be secured using adhesive or overmoulding for example, to avoid the need for through bores in the rigid components (the enlarged regions 124, rigid element 201, and connector 207) In an alternative embodiment, both rigid parts and filaments could be made from the same material, such as polyethylene, so that they could be chemically bonded. This creates a strong bond and avoids the need for knots in the filaments.

Figure 19:
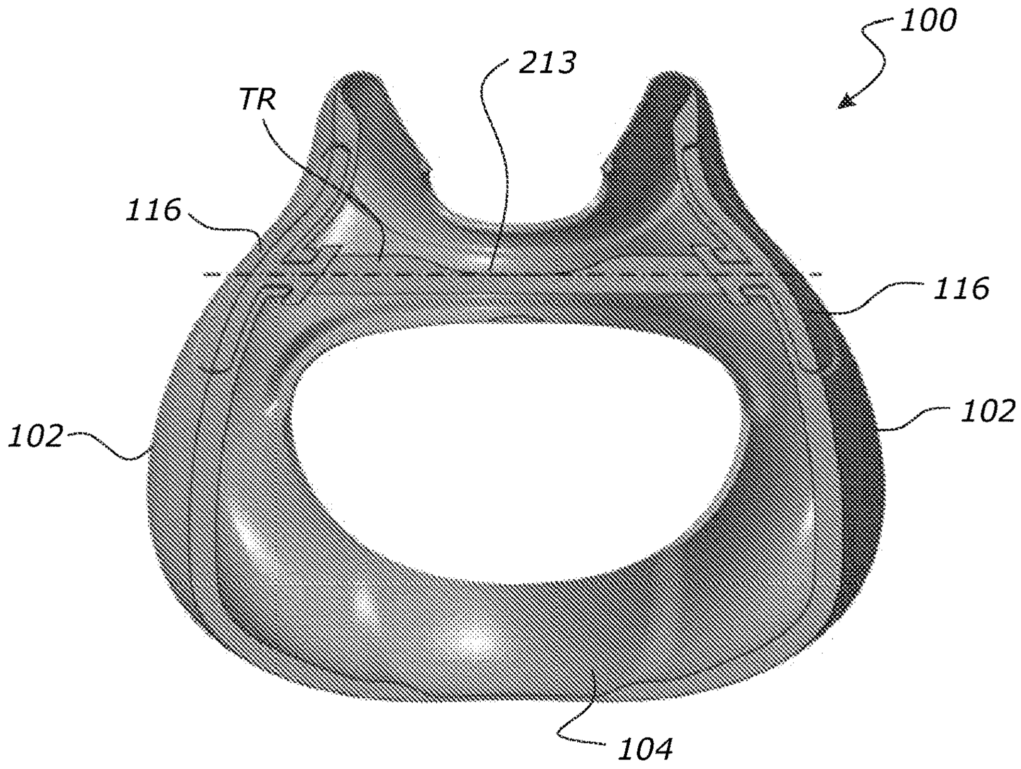
FIG. 19 is a front view of another embodiment of a patient interface in accordance with this disclosure, comprising another tether.

Referring now to FIG. 19, a tether T is provided which is similar to the embodiment of FIG. 10 described above, comprising a ribbon. The ribbon has substantially flat front and rear surfaces TF, TR. In this embodiment the ribbon may be of oblong transverse cross section over a substantive part of its length, and in this embodiment across all of its length between the side supports 116.

In this embodiment the upper margin of the tether T comprises a centrally located recess 213 in the form of a cut-out being a narrower central portion of the tether T, to provide additional clearance between the tether T and the nose of the patient.

Figure 20:
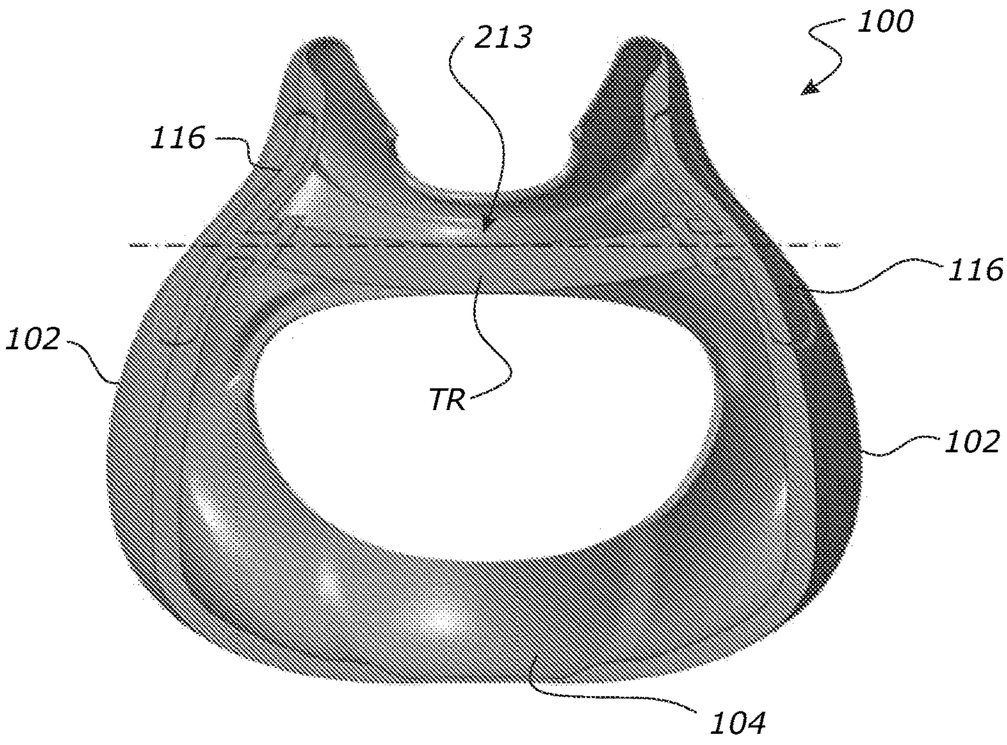
FIG. 20 is a front view of another embodiment of a patient interface in accordance with this disclosure, comprising another tether.

Referring now to FIG. 20, another tether T is provided similar to the embodiment of FIG. 10. In this embodiment, the tether T is arcuate, being curved along its length when viewed from the front. Again, this provides a recess 213 providing additional clearance between the central portion of the tether T and the nose of the user, by lowering the central portion of the tether T relative to the top of the cushion 100.

Figure 21A:
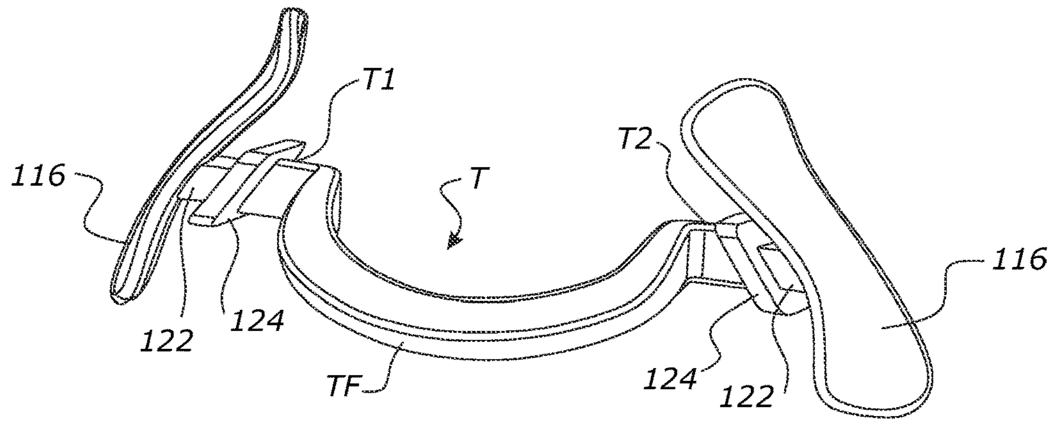
FIG. 21*a* is a perspective view of another embodiment of a tether and side supports in accordance with this disclosure, with FIGS. 21*b* and 21*c* being part sectional plan and side views respectively of the interior of a patient interface comprising the tether and side supports.
Figure 21B:
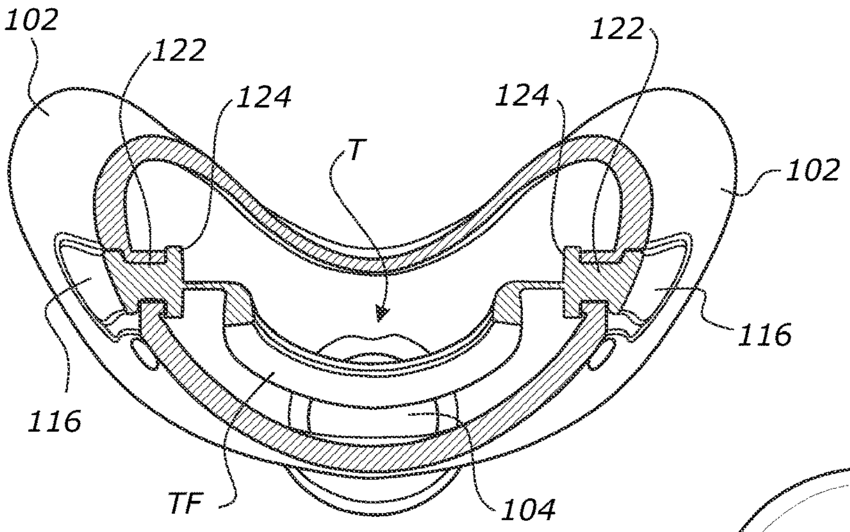
Figure 21C:
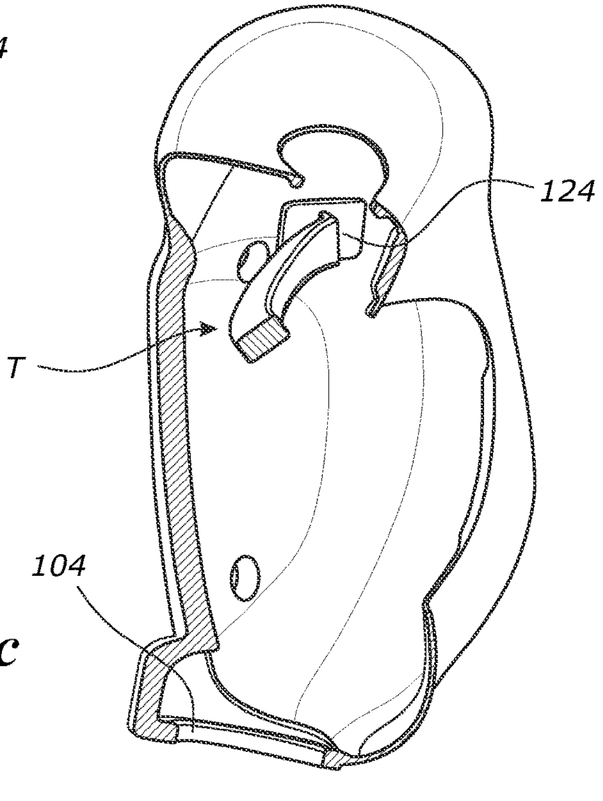

Referring to FIG. 21, an embodiment is shown having an arcuate tether T similar to that described above in FIG. 20. In this embodiment the arcuate tether T has a thicker cross section, and a sharper curvature between the enlarged regions 124. The arcuate tether is also inclined downwardly when viewed from the front and side. This configuration provides clearance between the tether T and the nose of the patient. The thicker cross section of this tether T reduces the flexibility of the tether T.

Figure 22A:
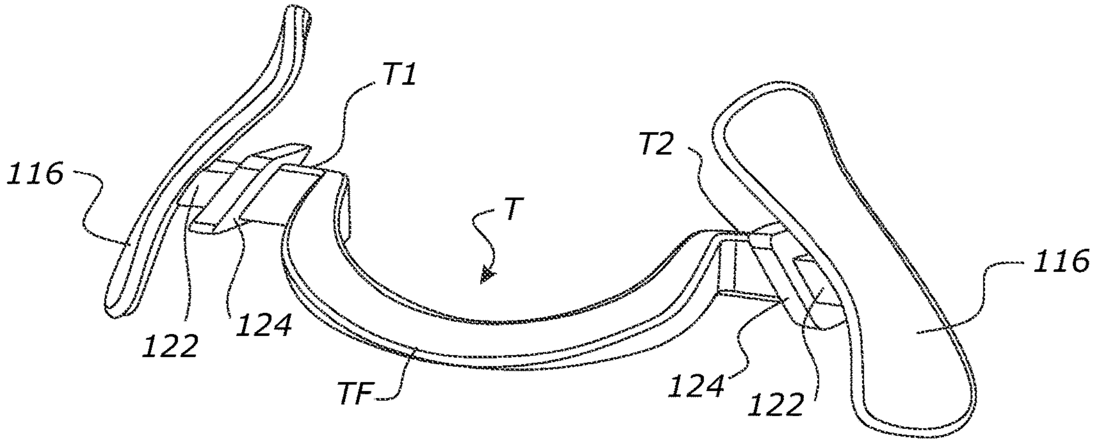
FIG. 22*a* is a perspective view of another embodiment of a tether and side supports in accordance with this disclosure, with FIGS. 22*b* and 22*c* being part sectional plan and side views respectively of the interior of a patient interface comprising the tether and side supports.
Figure 22B:
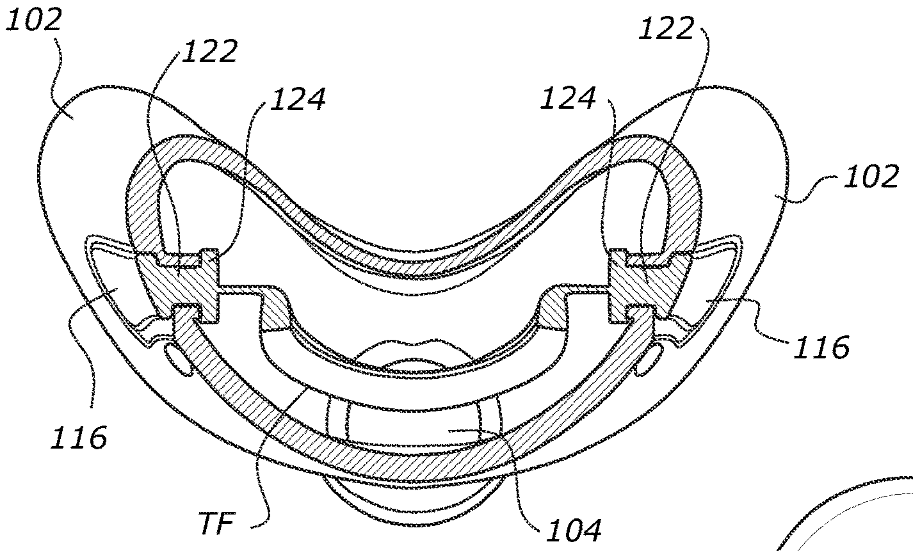
Figure 22C:
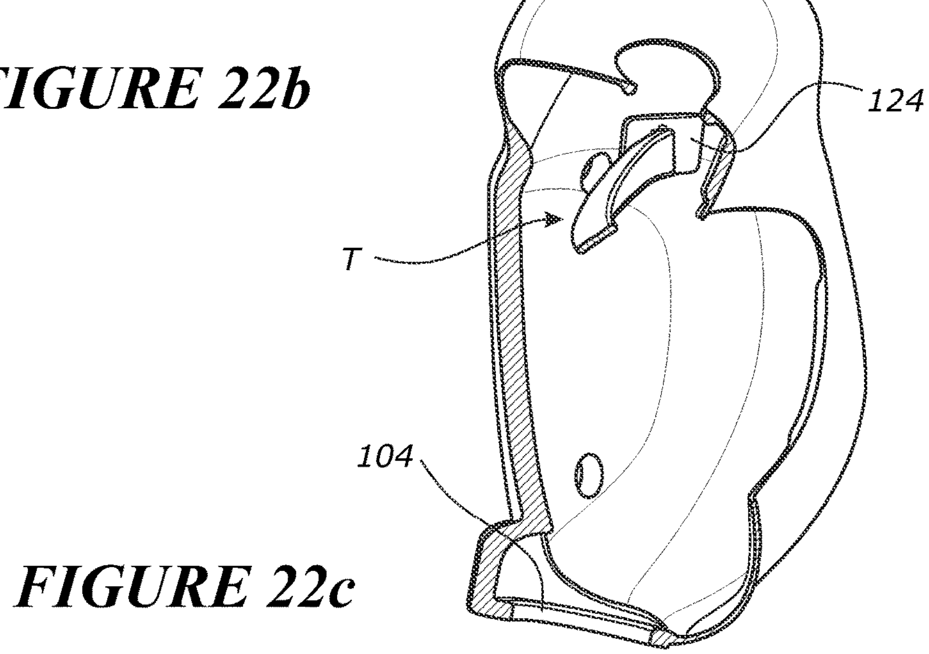

Referring to FIG. 22, an embodiment is shown having an arcuate tether T similar to that described in FIG. 20. In this embodiment the arcuate portion of the tether T is of variable shape and/or thickness cross section along its length. In particular a central portion of the tether T is thinner than the lateral portions of the tether T, so that the central portion has increased flexibility. This embodiment therefore provides a tether T having variable flexibility along its length.

Figure 23:
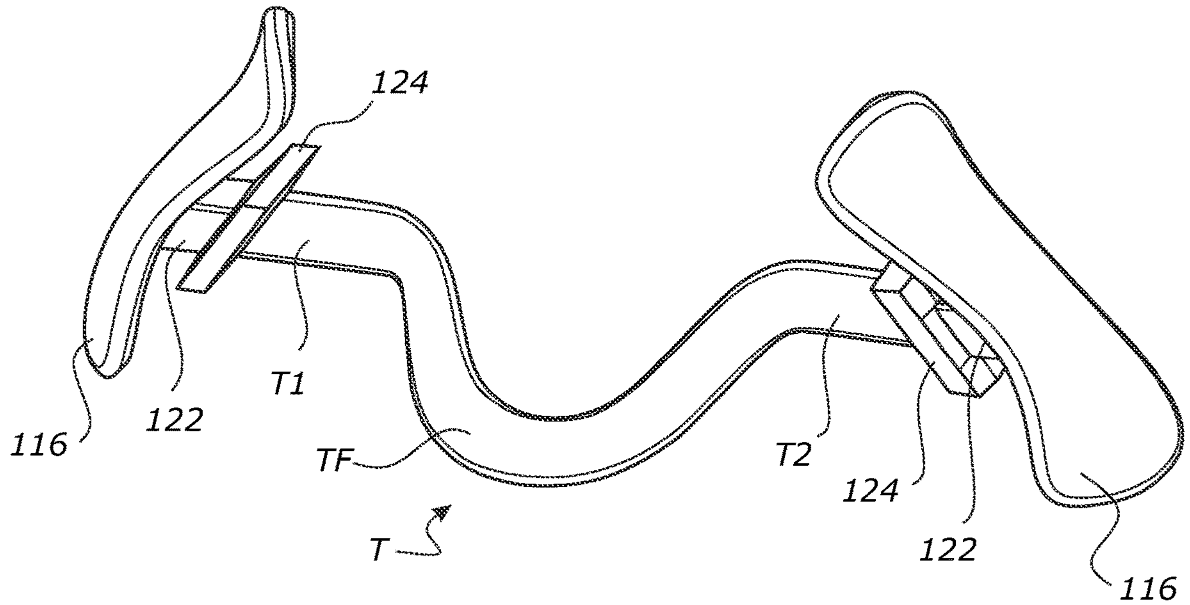
FIG. 23 is a perspective view from the front of another embodiment of a patient interface in accordance with this disclosure, comprising another tether.
Figure 24A:
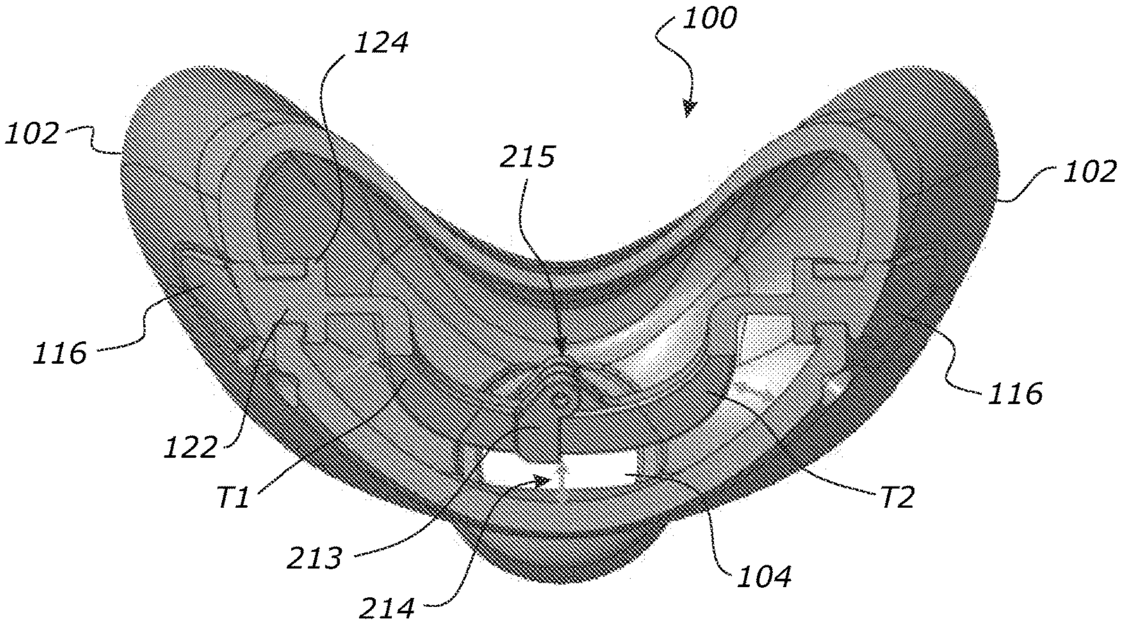
FIG. 24*a* is a part sectional plan view of another embodiment of a patient interface in accordance with this disclosure, comprising another tether, showing the tether in a resting condition.
Figure 24B:
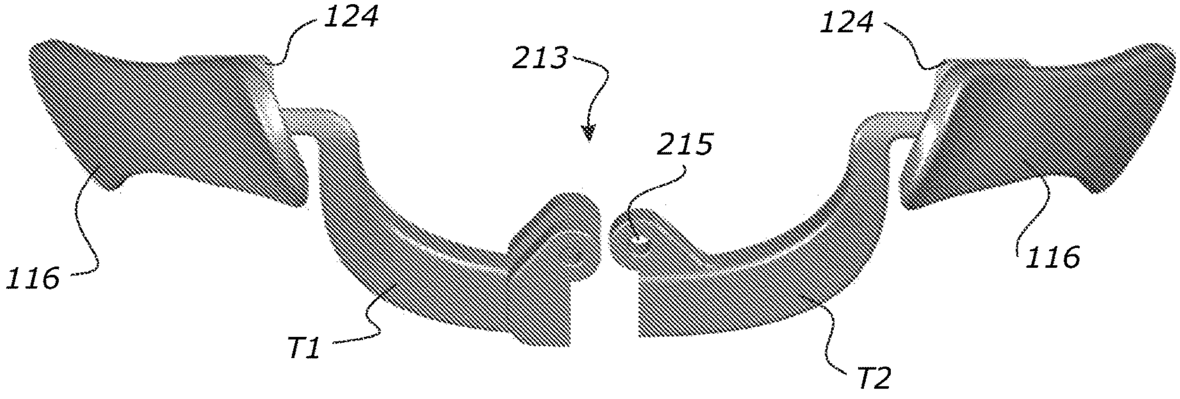
FIGS. 24*b* and 24*c* are respectively exploded front and plan views of the tether in a resting condition.
Figure 24C:
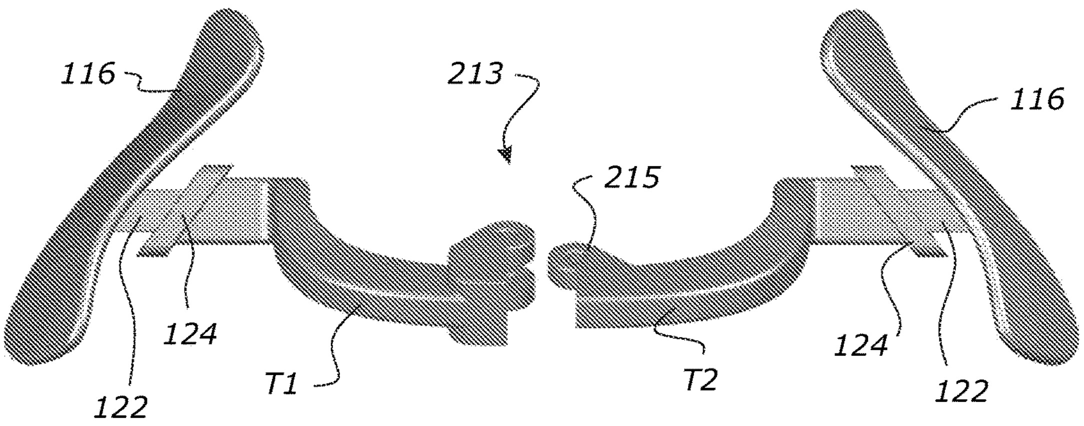
Figure 24D:
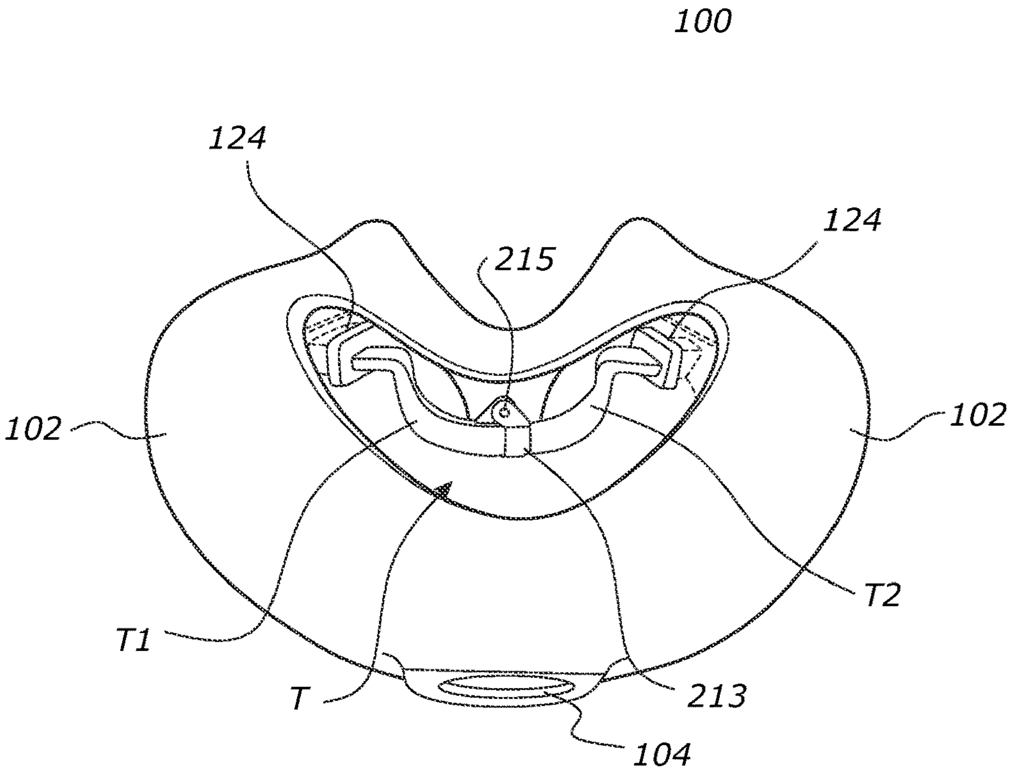
FIGS. 24*d* and 24*e* are views from underneath the patient interface, respectively showing the tether in expanded and collapsed conditions.
Figure 24E:
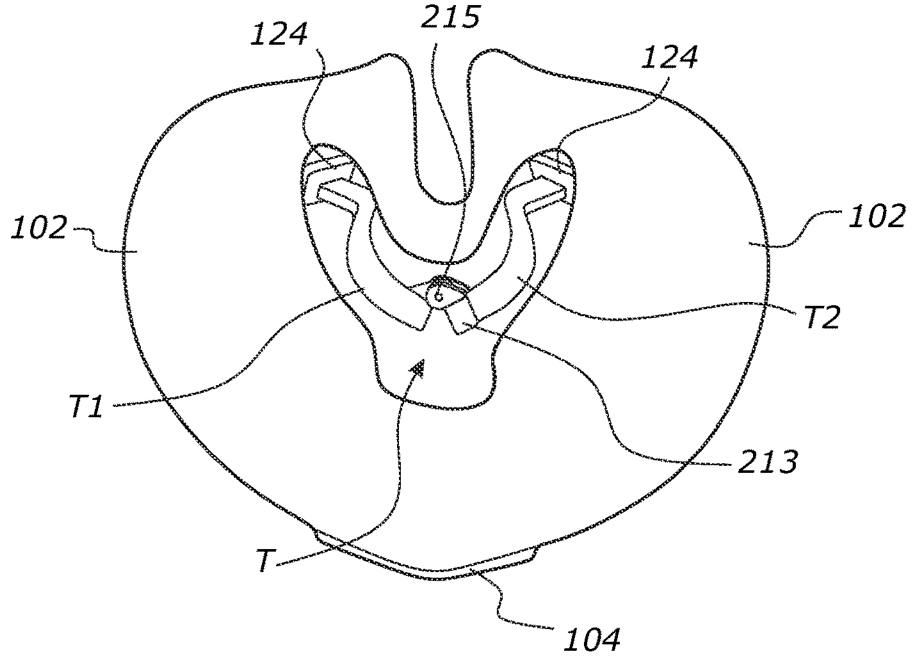
Figure 25A:
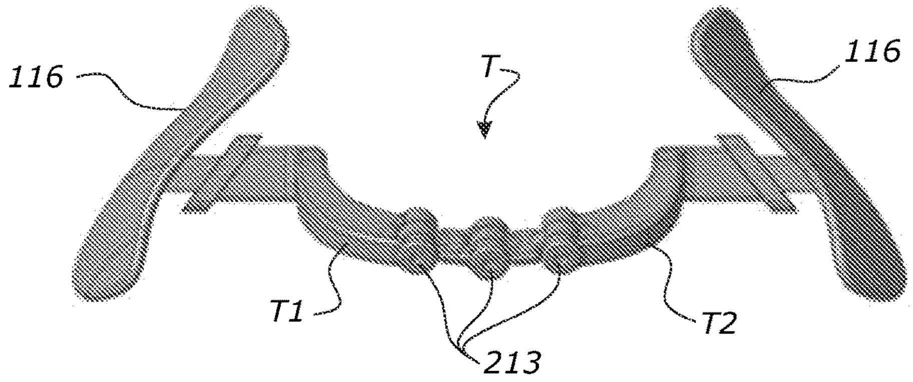
FIGS. 25*a* and 25*b* are front and plan views of another embodiment of the tether of FIG. 24*a*, with the tether in a resting condition.
Figure 25B:
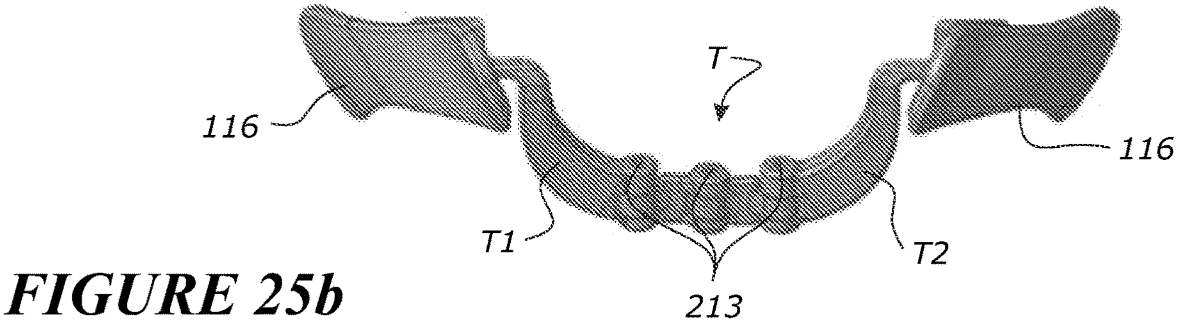
Figure 25C:
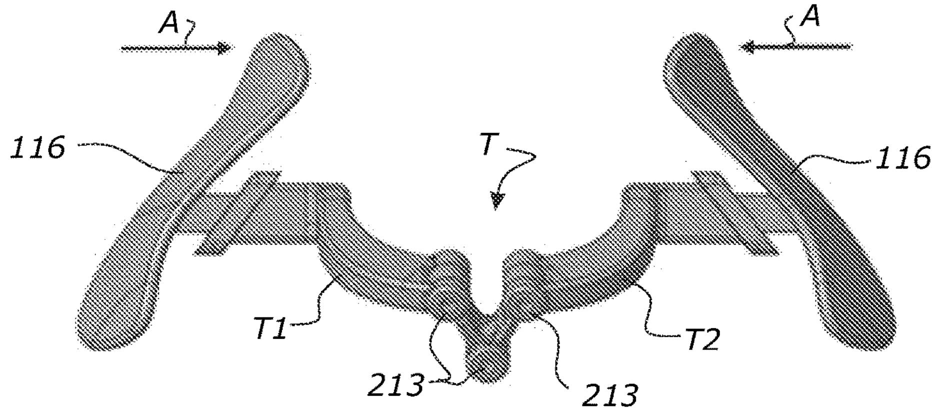
FIGS. 25*c* and 25*d* are front and plan views of the tether in a collapsed condition.
Figure 25D:
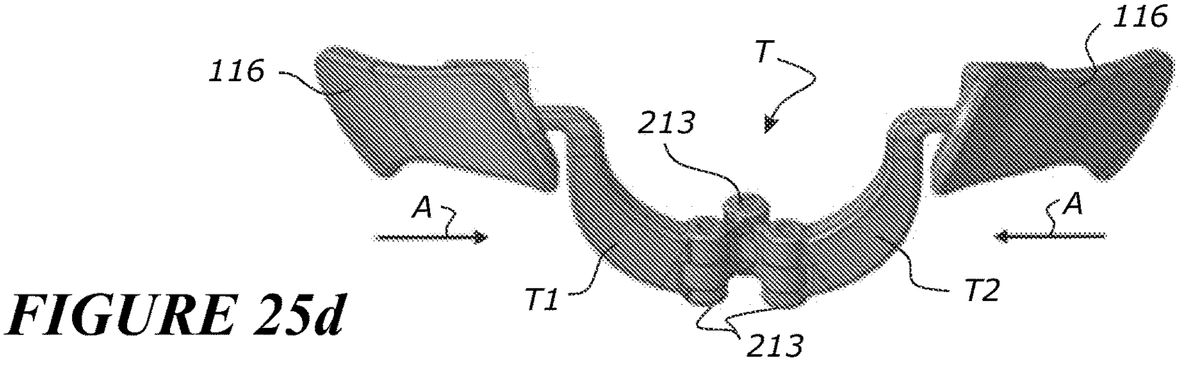

Referring to FIG. 23, an embodiment is shown having an arcuate tether T similar to that described in FIG. 22. In this embodiment the arcuate portion of the tether T is relatively thin along its entire length, such that the entire arcuate portion is relatively flexible, and the flexibility is substantially the same along its length.

Referring to FIG. 24, an embodiment is shown having an arcuate tether T that is similar to that described in FIG. 21, being an arcuate tether T having a relatively thick cross section. In this embodiment the tether T is provided with a hinge 213 which in this example comprises a single pivot axis 215, and which is located substantially centrally in the tether T. The hinge 213 divides the tether T into two tether side portions T1, T2. During side-sleeping, the force from the cushion side wall 102 causes the hinge 213 to open. As the hinge 213 opens, the ends of the arcuate tether side portions T1, T2 rotate towards each other to reduce the effective length of the tether T. The tether T can therefore move from a rest condition with the hinge 213 closed as shown in FIG. 24*a*, to a collapsed condition with the hinge 213 open as can be seen in FIG. 24*e*. The arcuate shape of the tether T ensures that there is a clearance between the rear surfaces of the tether T and hinge 213 and the face of the patient, and also a clearance 214 between the front surfaces of the tether T and hinge 213 and the front part of the cushion 100.

Figure 15A:
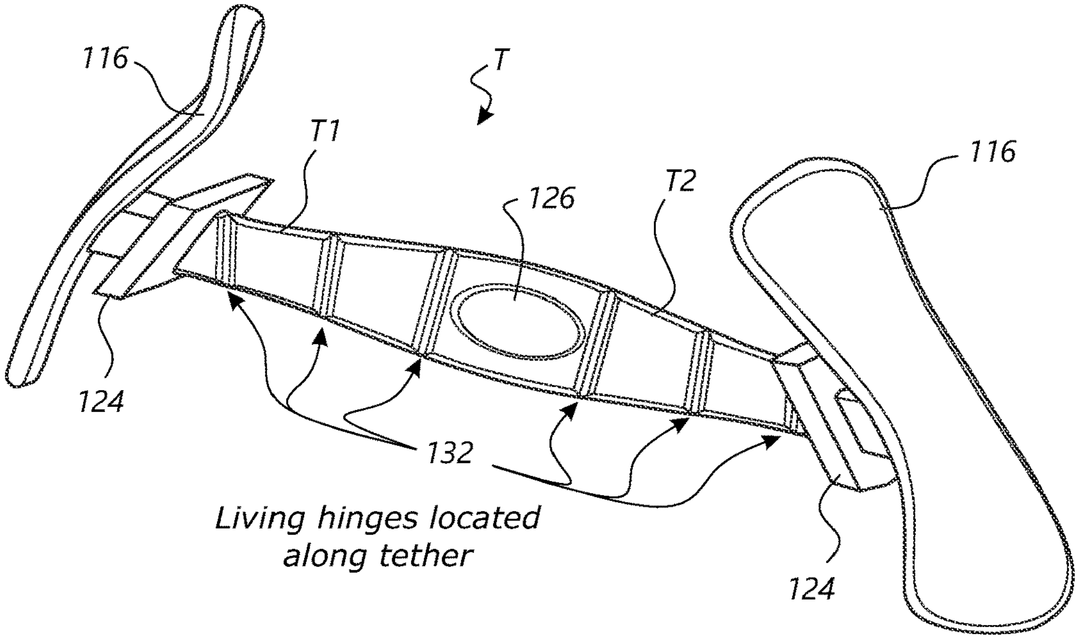
FIG. 15*a* is a perspective view of another embodiment of a tether and side supports in accordance with this disclosure, with FIG. 15*b* being a part sectional view of the interior of a patient interface comprising the tether and side supports, and FIGS. 15*c* and 15*d* being plan and front views.
Figure 15B:
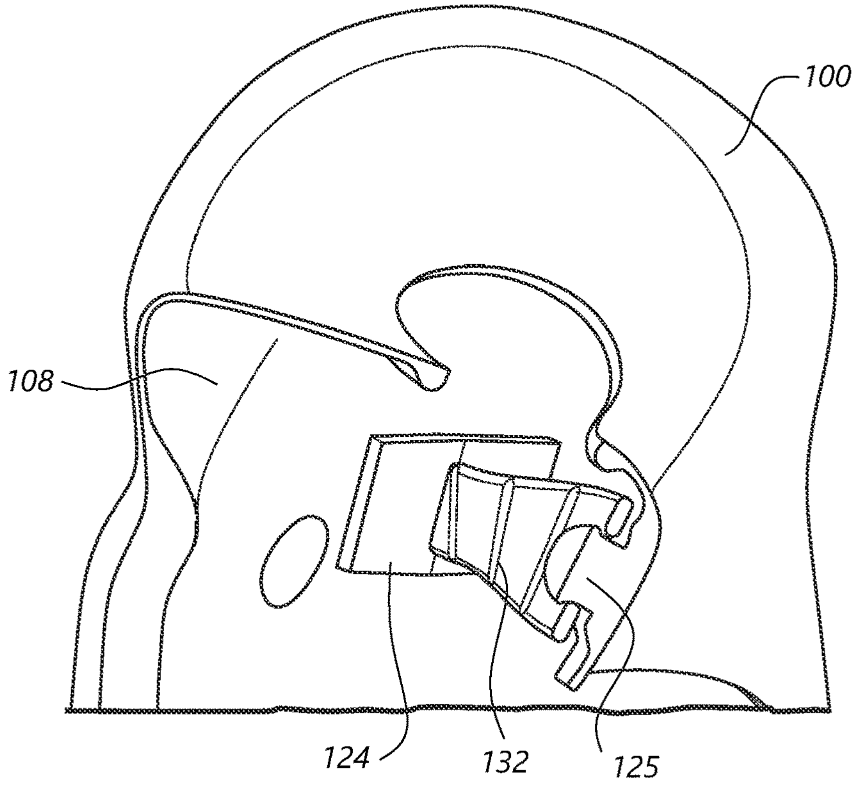
Figure 15C:
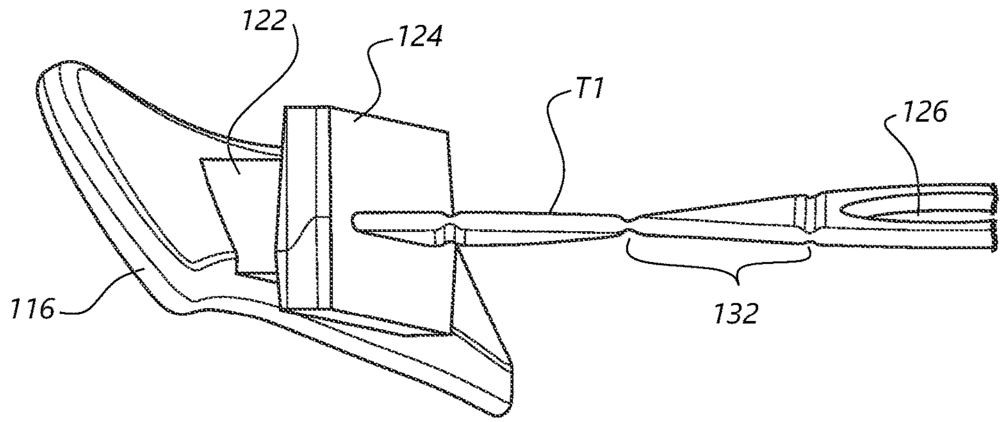
Figure 15D:
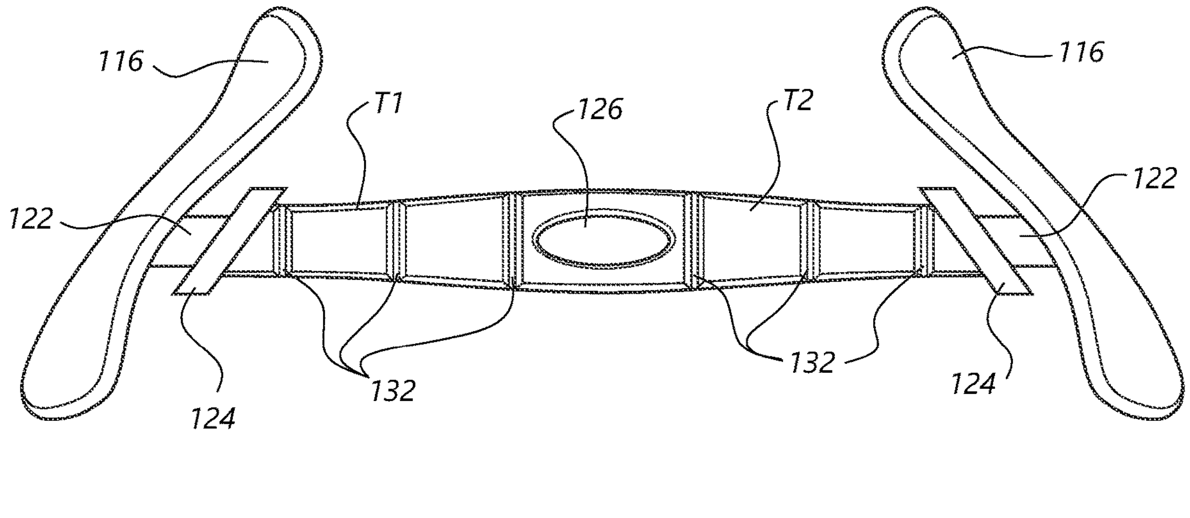

Hinge 213 may comprise a separate component or assembly to which the remainder of the tether T is attached, or may comprise, a living hinge, integral with the tether side portions T1, T2 (see also the embodiment of FIG. 15*a*).

Referring to FIG. 25, an embodiment is shown having an arcuate tether T that is similar to that described in FIG. 24. In this embodiment, a plurality of hinges 213 are provided. In the illustrated embodiment three hinges 213 are provided. This allows the opposed ends of the arcuate tether T to move towards each other in a linear motion indicated by the arrows A of FIGS. 25*c*, 25*d*, minimising rotation of the ends of the tether T.

Figure 26A:
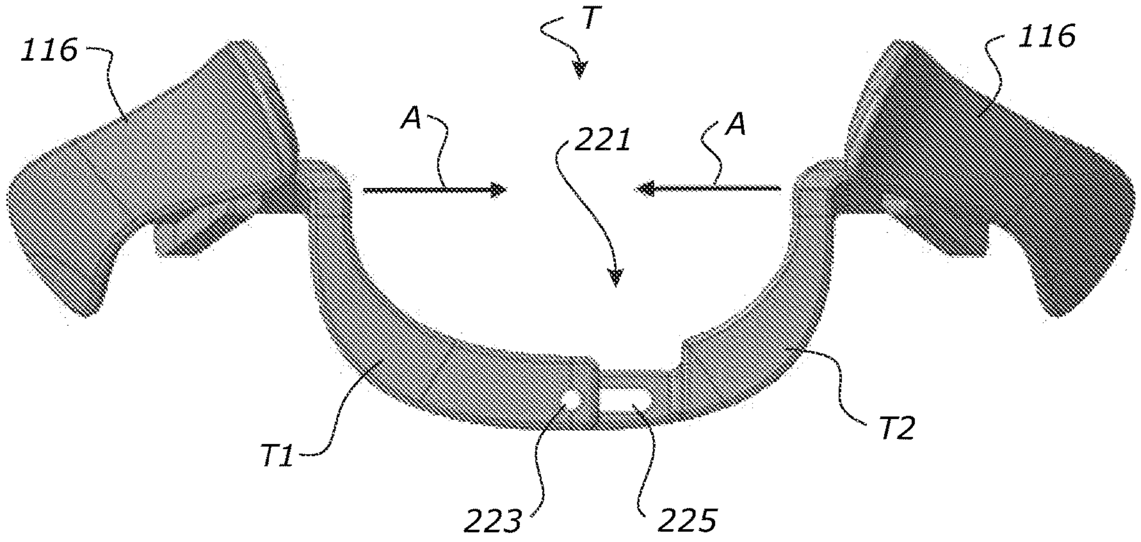
FIGS. 26*a* and 26*b* are front views of another embodiment of a tether in accordance with this disclosure, with the tether in resting and collapsed conditions respectively.
Figure 26B:
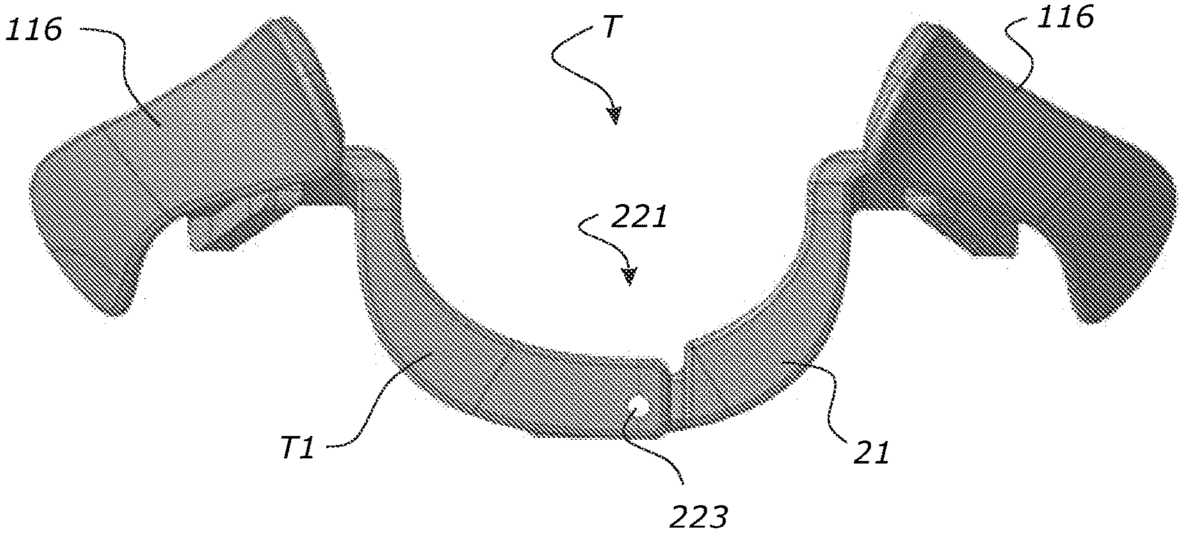

Referring now to FIG. 26, an embodiment is shown having an arcuate tether T that is similar that described in FIG. 21. In this embodiment, tether T comprises a length adjuster 221 at a central portion of the tether T. In this embodiment the tether T comprises two tether side portions T1, T2. The length adjuster 221 in this embodiment comprises a sliding mechanism comprising a pin 223 on one tether side portion T1, slidingly received in a slot 225 on the other tether side portion T2. FIG. 26*a* shows the tether T in a rest condition with the pin 223 at one end of the slot 225 such that the tether T has a first length. During side sleeping, the pin 223 slides along the slot 225 towards the other end of the slot 225 in the direction of arrows A, shortening the tether T to a second length. Length adjuster 221 allows the two tether side portions T1, T2 to move towards one another, without rotation of the tether side portions T1, T2.

Figure 27A:
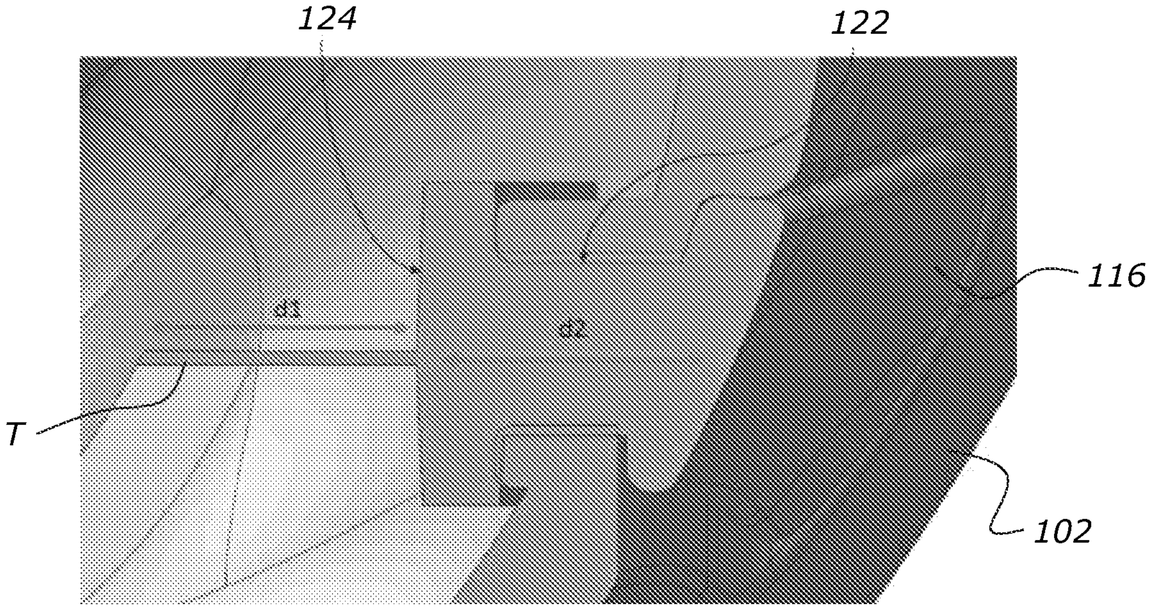
FIG. 27*a* is an enlarged sectional view of the tether and lateral mount of the patient interface of FIG. 1.

Referring now to FIG. 27, FIG. 27*a* shows the tether T of FIGS. 6 to 11, annotated to show two dimensions d1 and d2. Each side support 116 is secured to the tether T itself, via a respective mounting post 122. Each mounting post 122 extends through a respective aperture in the cushion side walls 102, the mounting posts 122 having substantially the same shape and diameter as the apertures. Each mounting post 122 comprises an enlarged region 124 that engages the interior surface of the cushion side walls 102 to securely locate the tether T against the interior surface of the cushion 100.

Figure 27B:
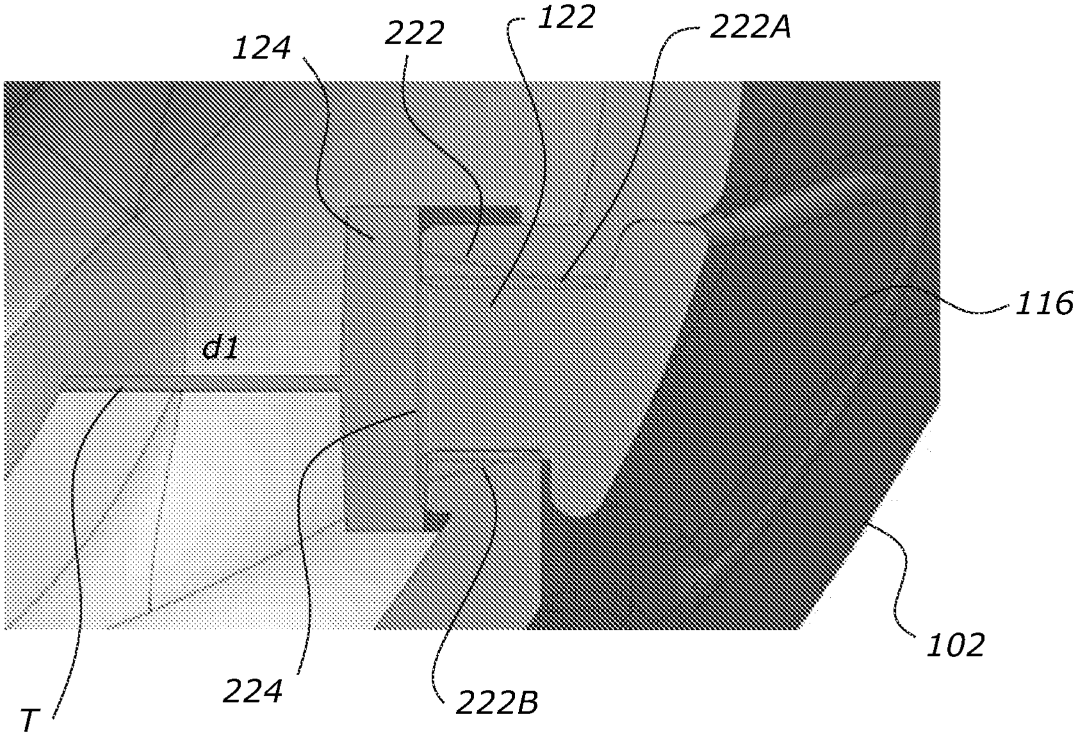
FIG. 27*b* is a view similar to FIG. 27*a*, showing a modified tether and lateral mount superimposed on the tether and lateral mount of FIG. 27*a*.

In the embodiment of FIG. 6, the mounting post 122 is substantially uniform when viewed in cross section through the cushion wall 102, having straight parallel sides 122A, 122B. This can be seen in FIG. 27*a*. FIG. 27*b* schematically shows an alternative shape mounting post 222 in which the mounting post 222 tapers inwardly, as it passes through the cushion side wall 102, the mounting post 222 therefore having inclined side walls 222A, 222B. The mounting post 222 therefore comprises a wider end being an enlarged region 224 that engages the inside surface of the cushion side wall 102.

As can be seen in FIG. 27*b*, the enlarged region 224 can be of smaller diameter than the enlarged region 124 described above, and can also provide an improved seal with the cushion side wall 102.

The enlarged region 224 can also be configured to be substantially flush with the inside surface of the cushion side wall 102, reducing the combined length of the enlarged region 124 and mounting post 122, such that the dimension d1 is increased. This allows for a longer buckling distance of the tether T.

Figure 28A:
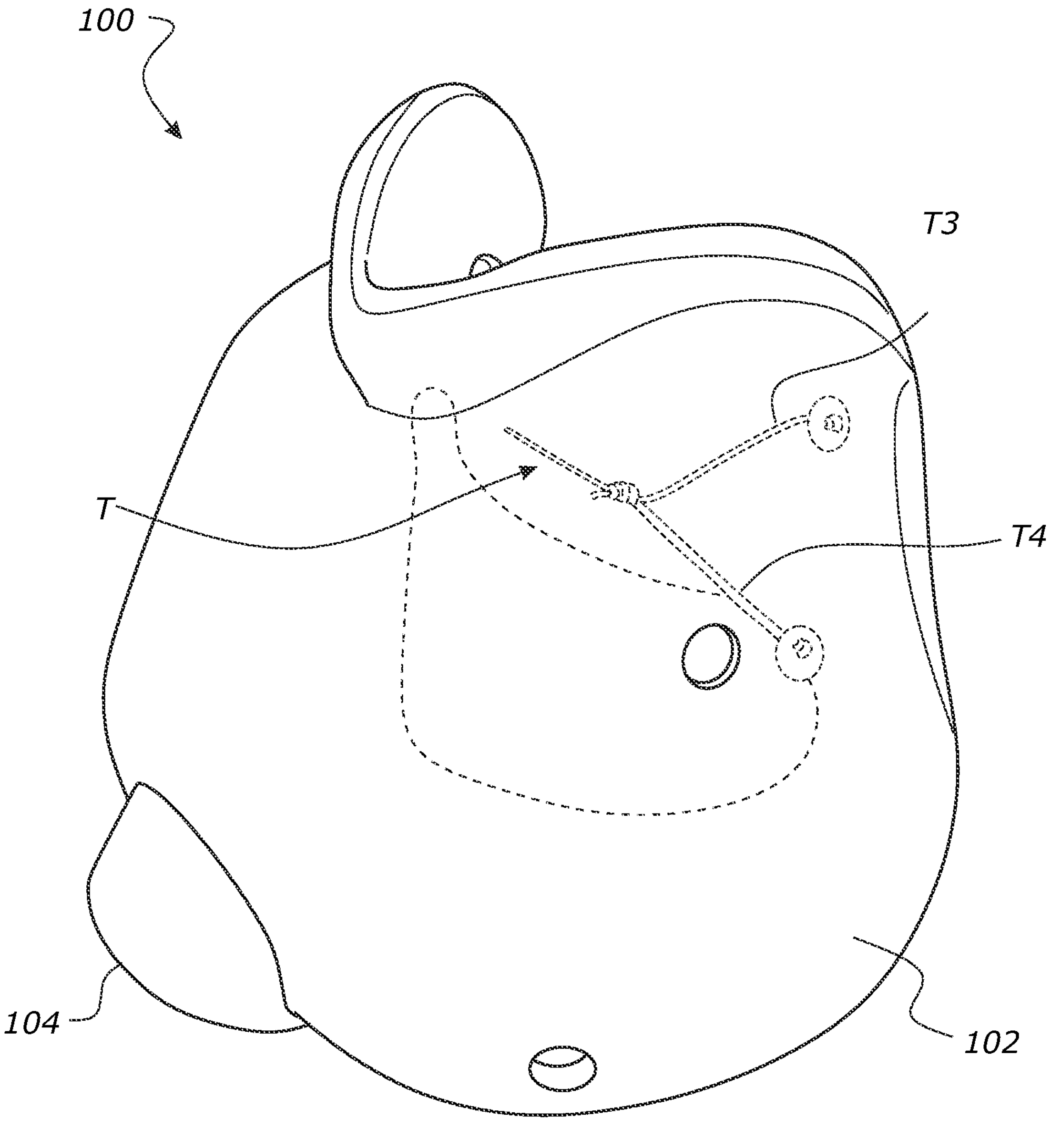
FIG. 28*a* is a perspective view from the front of another patient interface in accordance with this disclosure.
Figure 28B:
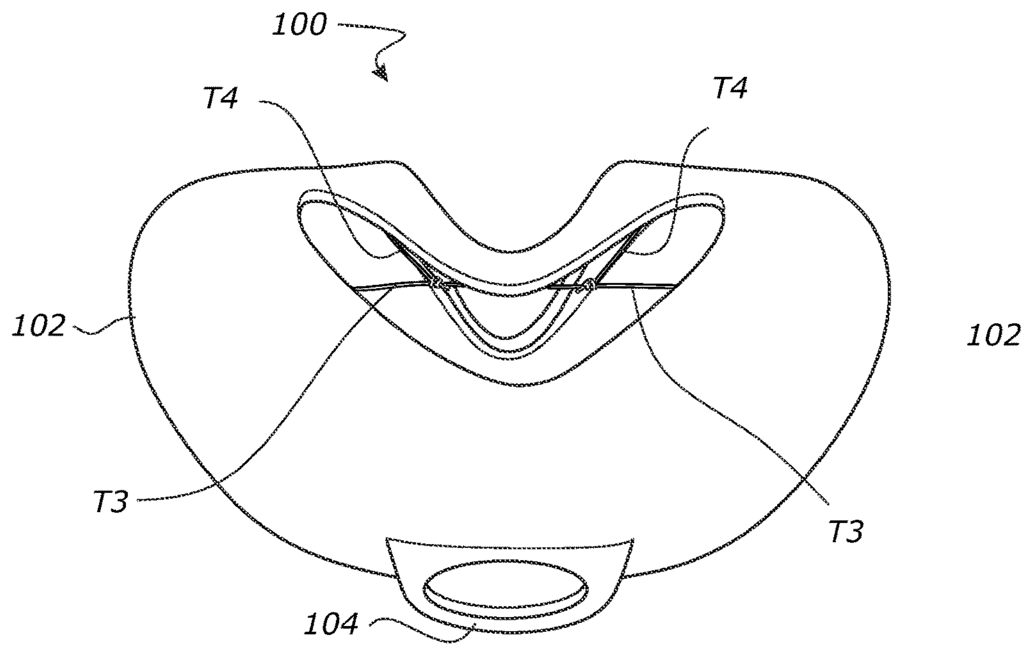
FIG. 28*b* is a perspective view of the patient interface from underneath.
Figure 28C:
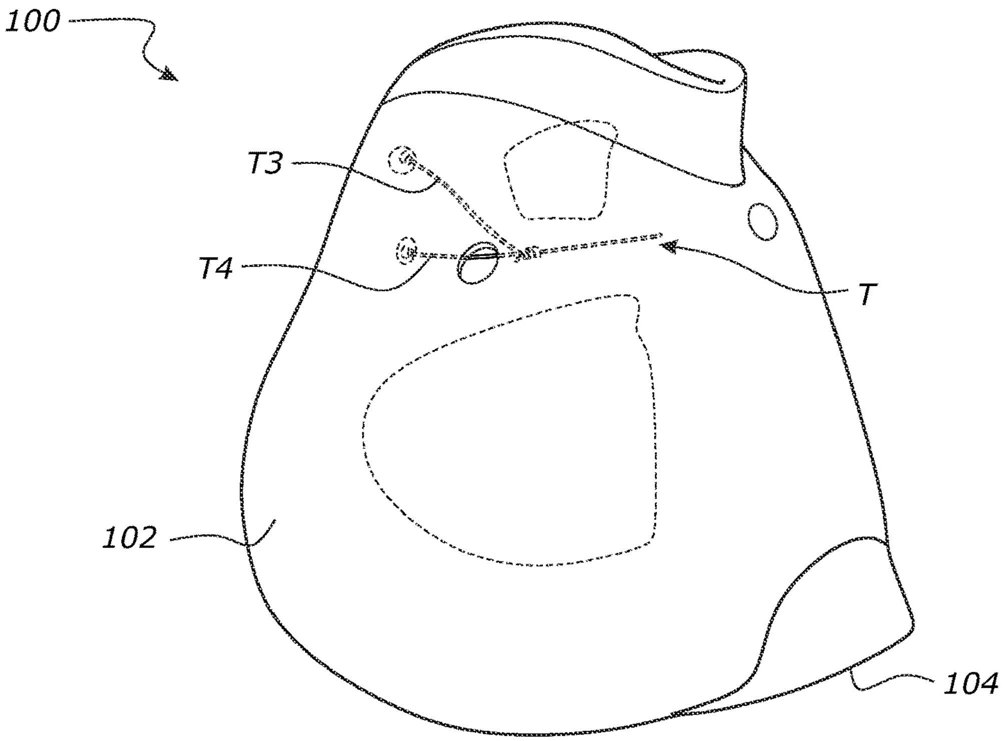
FIG. 28*c* is a view of the patient interface from the side.

Referring now to FIG. 28, in this embodiment tether T comprises a central portion, each end of which bifurcates so that each end comprises a pair of tether end portions T3, T4. Each pair of tether end portions T1, T2 is arranged in a triangular configuration, with a proximal end of each tether end portion T1, T2 being connected to the tether central portion. The distal end of each tether end portion T1, T2 are mounted in spaced apart relationship on the cushion side wall 102. Consequently, the tether T is mounted to the cushion side wall 102 using a pair of spaced apart connection points. This configuration can reduce ballooning of the cushion 100.

Figure 29A:
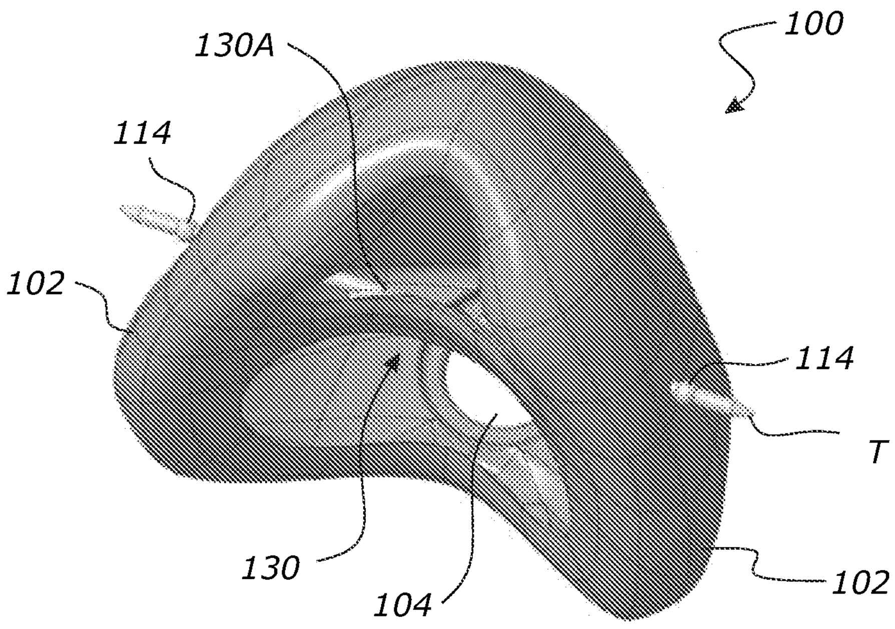
FIG. 29*a* is a perspective view from the rear of another patient interface in accordance with this disclosure.
Figure 29B:
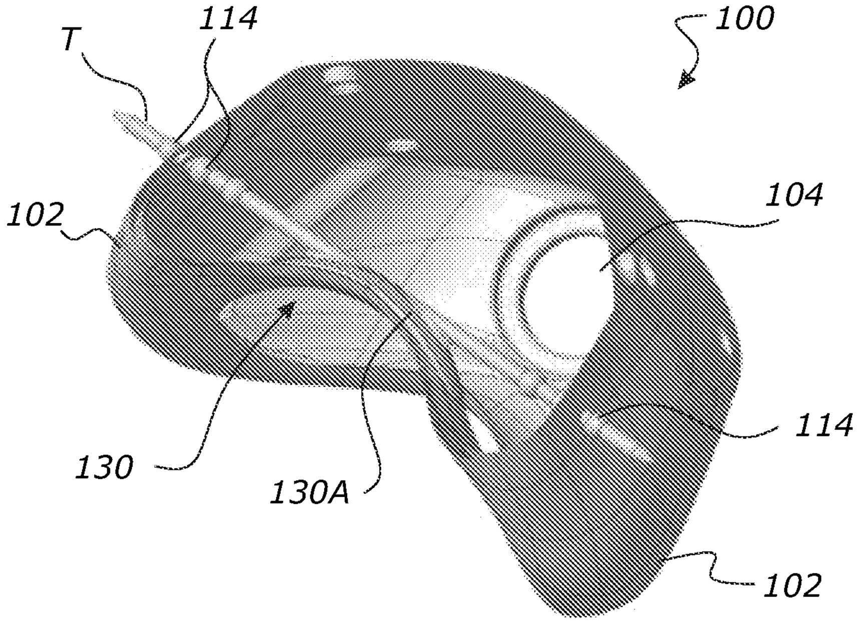
FIG. 29*b* is a perspective part sectional view of the patient interface from above.

Referring now to FIG. 29, an embodiment is disclosed which is similar to that of FIG. 4. In this embodiment a substantially straight tether T is provided. Each end of the tether T comprises a plurality of spaced apart retainers 114. Each retainer 114 comprises an enlarged region of the tether T. The cushion side wall 102 on each side of the cushion 102 is sandwiched between a pair of retainers 114. In this embodiment each end of the tether T is provided with three retainers 114, thus providing two different pairs of retainers 114 between which the cushion side wall 102 can be sandwiched. The effective length of tether T is therefore adjustable in this embodiment, such that the lateral spacing between the cushion side walls 102 can be adjusted by selecting different pairs of retainers 114. Such a tether T can be used with different sized cushion sizes, for example supplied in a kit with a plurality of different sized cushions 100. Alternatively, the adjustability allows for a single cushion size to be provided that can be adjusted to fit different size patients.

The central part of the tether T of FIG. 29 widens into a central support region 130A that is positioned to rest adjacent the upper lip of the patient. In this embodiment the central support region 130A may function as a central tether mount 130, similar to the embodiment of FIG. 16, where the central tether mount 130 is attached to the upper lip contacting part of the cushion 100. This offers support across the top lip area by increasing contact area to minimise or reduce the higher forces that would arise from a smaller contact area.

Figure 30A:
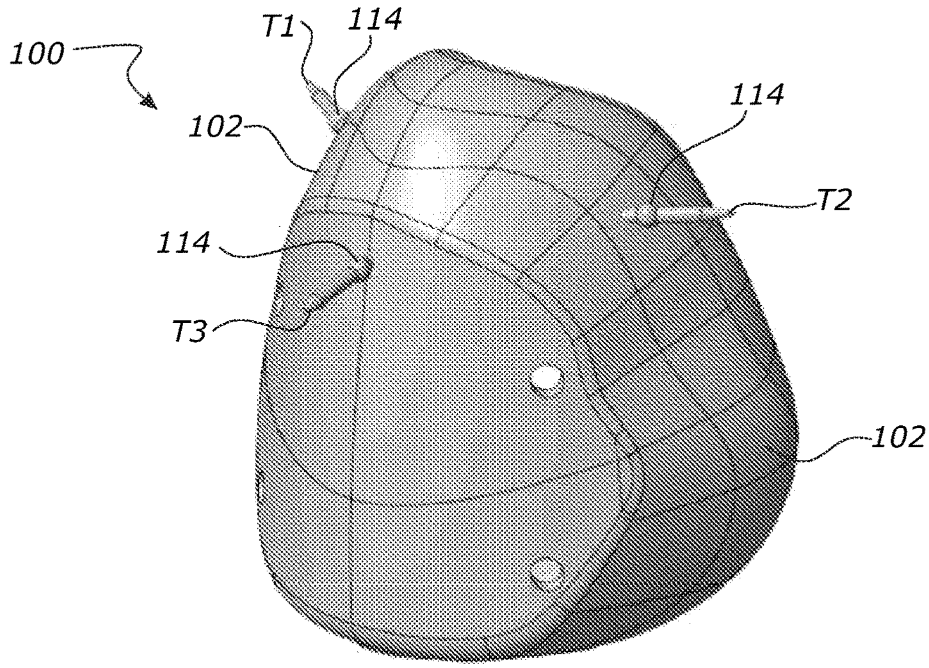
FIG. 30*a* is a perspective view from the front of another patient interface in accordance with this disclosure.
Figure 30B:
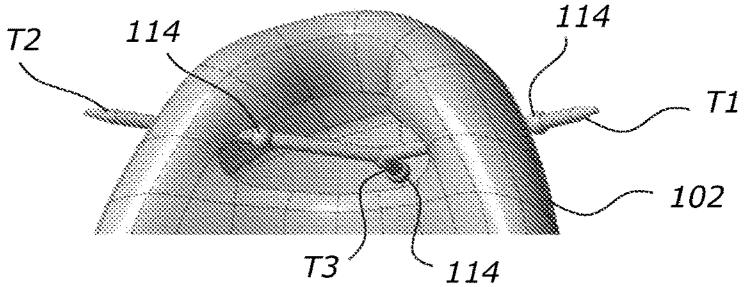
FIG. 30*b* is a perspective view of an upper part of the patient interface from the rear.
Figure 30C:
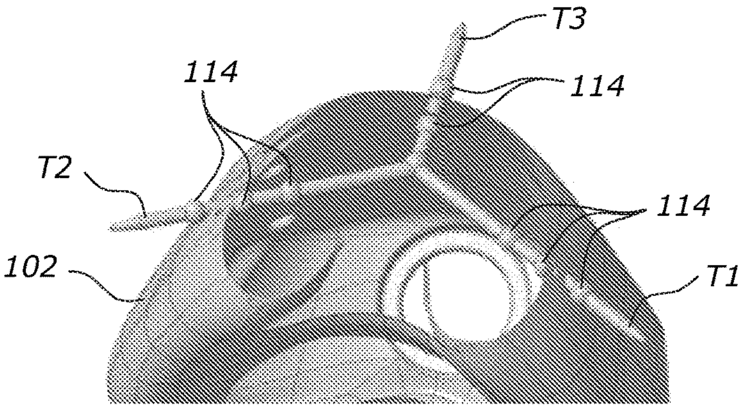
FIG. 30*c* is a perspective part sectional view of the patient interface from above.

Referring now to FIG. 30, another embodiment in accordance with this disclosure comprises a tether T with a similar structure to that of FIG. 29. The tether T in this example also has multiple retainers 114 to allow adjustment between the tether T and the cushion side walls 102. In this embodiment, the tether T comprises three tether portions T1, T2, T3, each having a proximal end that intersects the others, each having a distal end that is secured to the cushion 100. Two of the tether portions T1, T2 are secured to respective cushion side walls 102, the third tether portion T3 being secured to the front of the cushion 100, above the upper lip portion of the cushion 100. This configuration triangulates the mounting of the tether T to the cushion 100 across three mounting points, creating a larger space in the central part of the tether T between the tether T and the upper lip of the patient, and minimising any contact or interference with the user's face or nose.

Embodiments in accordance with this disclosure provide a patient interface which is collapsible, or at least partially deformable. The provision of a tether in accordance with this disclosure serves to at least partially control that deformation, for example when a patient is side sleeping, but also in any other situation where the patient interface may be subject to forces that would otherwise deform it, for example under higher pressures or flow rates. The patient interface may comprise a rigid frame or yoke, on which the cushion is mounted, or in preferred embodiments such a frame or yoke may be omitted. The cushion 100 in accordance with this disclosure may therefore be relatively soft and flexible, so that the cushion 100 can relatively easily deform. Such a cushion 100 may provide for improved patient comfort, and/or an improved seal with the patient's face. Because of the provision of the tether T, the cushion could be more flexible, and/or softer, and/or more deformable, than prior art cushions.

Tether T can be formed of a single material, or multiple materials, and/or a single length of material or multiple lengths wound, knitted or woven together. Tether T could therefore comprise a cord of multiple strands of material, or only a single strand of material. Tether T can be of a flexible, inextensible material such as nylon.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Where reference is used herein to directional terms such as 'up', 'down', 'forward', 'rearward', 'horizontal', 'vertical' etc., those terms refer to when the apparatus is in a typical in-use position, and are used to show and/or describe relative directions or orientations.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

The invention claimed is:

1. A patient interface for use with a respiratory support apparatus for delivering breathable gases to a patient, the patient interface comprising:

a cushion at least partially defining an internal cavity, the cushion comprising a pair of opposing cushion side walls and a sealing flange arranged to seal against a face of the patient;

a gases inlet in fluid communication with the internal cavity; and a tether;

wherein the tether extends substantially laterally across the cushion inside the internal cavity between the pair of opposing cushion side walls, the tether being mounted to the pair of opposing cushion side walls;

wherein the tether is configured to resist laterally outward movement of the pair of opposing cushion side walls; and wherein the tether and the pair of opposing cushion side walls are configured such that the tether extends across, but is spaced from, an upper lip region of the patient.

2. The patient interface of claim 1, wherein the tether is integral with the cushion.

3. The patient interface of claim 1, wherein the tether and the cushion are separate components.

4. The patient interface of claim 3, further comprising a pair of laterally spaced mounts on the cushion, the tether being secured to the cushion by the pair of laterally spaced apart mounts.

5. The patient interface of claim 1, wherein the pair of opposing cushion side walls are laterally spaced by a predetermined distance, the tether being configured to substantially maintain the predetermined distance.

6. The patient interface of claim 1, wherein the tether is configured to allow laterally inward movement of the pair of opposing cushion side walls.

7. The patient interface of claim 1, wherein the tether is inextensible under tensile forces.

8. The patient interface of claim 1, wherein the tether is collapsible under compressive forces.

9. The patient interface of claim 1, wherein the tether is inelastic.

10. The patient interface of claim 1, wherein the cushion comprises a nasal bridge region and the tether is positioned below the nasal bridge region.

11. The patient interface of claim 1, wherein the cushion comprises a pair of side of nose portions and the tether is positioned below the side of nose portions.

12. The patient interface of claim 11, wherein the side of nose portions are provided on, or comprise part of, the pair of opposing cushion side walls.

13. The patient interface of claim 1, wherein the tether is rigid, or at least comprises a rigid portion.

14. The patient interface of claim 1, wherein the tether comprises any one of:

a filament;

a wire;

one or more fibres;

a ribbon;

string; and a braided element.

15. The patient interface of claim 1, wherein the tether is formed from any one of:

plastic;

metal;

silicone;

a woven material;

a knitted material; and a braided material.

16. The patient interface of claim 1, wherein the tether comprises a circular or elliptical transverse cross section.

17. The patient interface of claim 1, wherein the tether comprises a non-circular transverse cross section.

* * * * *